United States Patent
Takata et al.

(10) Patent No.: US 12,257,616 B2
(45) Date of Patent: Mar. 25, 2025

(54) CONTROL SYSTEM AND METHOD FOR TAPERED STRUCTURE CONSTRUCTION

(71) Applicant: Keystone Tower Systems, Inc., Denver, CO (US)

(72) Inventors: Rosalind K. Takata, Denver, CO (US); Eric D. Smith, Denver, CO (US); Loren Daniel Bridgers, Golden, CO (US); Daniel Ainge, Boulder, CO (US); Alexander H. Slocum, Bow, NH (US)

(73) Assignee: Keystone Tower Systems, Inc., Denver, CO (US)

( * ) Notice: Subject to any disclaimer, the term of this patent is extended or adjusted under 35 U.S.C. 154(b) by 263 days.

(21) Appl. No.: 17/825,210

(22) Filed: May 26, 2022

(65) Prior Publication Data

US 2022/0297175 A1    Sep. 22, 2022

Related U.S. Application Data

(63) Continuation of application No. 16/208,831, filed on Dec. 4, 2018, now Pat. No. 11,364,527, which is a
(Continued)

(51) Int. Cl.
*B21C 37/12* (2006.01)
*B21C 37/18* (2006.01)
*B23K 9/032* (2006.01)

(52) U.S. Cl.
CPC .......... *B21C 37/185* (2013.01); *B21C 37/122* (2013.01); *B21C 37/124* (2013.01);
(Continued)

(58) Field of Classification Search
CPC ... B21C 37/122; B21C 37/124; B21C 37/125; B21C 37/126; B21C 37/128;
(Continued)

(56) References Cited

U.S. PATENT DOCUMENTS 1,498,176 A    6/1924   Lachman
1,659,792 A    2/1928   Thorsby et al.
(Continued)

FOREIGN PATENT DOCUMENTS

AU    2020200768    3/2022
CN    85105639      1/1987
(Continued)

OTHER PUBLICATIONS

Canadian IPO; Canadian Application No. 2,944,178; PCT No. US2015022648; Examiner's Report dated Apr. 9, 2021, 7 pages.
(Continued)

*Primary Examiner* — Edward T Tolan
(74) *Attorney, Agent, or Firm* — The Marbury Law Group, PLLC

(57) ABSTRACT

A control system for forming a tapered structure includes a sensor providing feedback for a machine for forming a tapered structure including at least three rolls having at least one bend roll and at least two guide rolls. The guide rolls may include rollette banks having a plurality of rollettes. The machine may also include an adjustment mechanism to position at least one of the rolls, where a diameter of the tapered structure being formed is controlled by relative positions of the rolls. The machine may also include a joining element to join edges of a stock of material together as it is rolled through the rolls to form the tapered structure. The control system may also include a controller to receive feedback from the sensor and to send a control signal based on the feedback to the adjustment mechanism for positioning at least one of the rolls.

13 Claims, 22 Drawing Sheets

Related U.S. Application Data continuation of application No. 14/228,481, filed on Mar. 28, 2014, now Pat. No. 10,189,064.

(52) U.S. Cl.
CPC .......... *B21C 37/128* (2013.01); *B23K 9/0325* (2013.01); *B21C 37/126* (2013.01)

(58) Field of Classification Search
CPC ... B21C 37/0803; B21C 37/18; B21C 37/185; B23K 9/0325
See application file for complete search history.

(56) References Cited

U.S. PATENT DOCUMENTS

| | | |
|---|---|---|
| 2,008,423 A | 7/1935 | Ritchie |
| 2,054,153 A | 9/1936 | Awbrey |
| 2,355,707 A | 8/1944 | De Boer |
| 2,412,678 A | 12/1946 | Goldman |
| 2,567,020 A | 9/1951 | Kueter |
| 2,584,074 A | 1/1952 | Wilkins et al. |
| 2,593,714 A | 4/1952 | Robinson et al. |
| 2,706,851 A | 4/1955 | Stout et al. |
| 2,991,740 A | 7/1961 | Eckhardt |
| 3,227,345 A | 1/1966 | Vilem |
| 3,300,042 A | 1/1967 | Gordon |
| 3,332,265 A | 7/1967 | Colas |
| 3,407,639 A | 10/1968 | Kehne |
| 3,472,053 A | 10/1969 | William |
| 3,606,783 A | 9/1971 | Lewis |
| 3,650,015 A | 3/1972 | Davis |
| 3,775,835 A | 12/1973 | Cauffiel et al. |
| 3,776,010 A | 12/1973 | Krakow |
| 3,808,862 A | 5/1974 | Tanaka et al. |
| 3,845,645 A * | 11/1974 | Gebauer ............... B21C 37/126 72/170 |
| 3,888,283 A | 6/1975 | Cauffiel |
| 3,991,597 A | 11/1976 | Krakow et al. |
| 3,997,097 A | 12/1976 | Embury |
| 4,082,211 A | 4/1978 | Embury |
| 4,147,454 A | 4/1979 | Willums et al. |
| 4,255,999 A * | 3/1981 | Davis ................... B21D 43/023 409/138 |
| 4,261,931 A | 4/1981 | Rothrock et al. |
| 4,367,640 A | 1/1983 | Heitzman et al. |
| 4,438,643 A * | 3/1984 | Menzel ............... B21C 37/124 72/49 |
| 4,640,453 A | 2/1987 | Oe et al. |
| 4,927,050 A | 5/1990 | Palazzo et al. |
| 4,945,363 A | 7/1990 | Hoffman |
| 5,063,969 A | 11/1991 | Snyder et al. |
| 5,139,603 A | 8/1992 | Kunz et al. |
| 5,180,095 A * | 1/1993 | Orth ..................... B23K 9/0286 228/9 |
| 5,301,869 A | 4/1994 | Toyooka et al. |
| 5,326,410 A | 7/1994 | Boyles |
| 5,573,716 A | 11/1996 | Jacobson |
| 5,862,694 A | 1/1999 | Horning |
| 5,865,053 A | 2/1999 | Abbey, III et al. |
| 5,868,888 A | 2/1999 | Don et al. |
| 5,957,366 A * | 9/1999 | Friedrich ............. B21C 37/122 228/9 |
| 6,306,235 B1 | 10/2001 | Henderson |
| 6,339,945 B2 | 1/2002 | Miller et al. |
| 6,364,141 B1 | 4/2002 | Ehrgott |
| 6,533,749 B1 | 3/2003 | Mitusina et al. |
| 6,732,906 B2 | 5/2004 | Andersen |
| 6,964,141 B2 | 11/2005 | Igarashi |
| 7,739,843 B2 | 6/2010 | Cortina-Cordero |
| 7,802,412 B2 | 9/2010 | Jensen |
| 8,146,320 B2 | 4/2012 | Seidel et al. |
| 8,196,358 B2 | 6/2012 | Shiraishi |
| 8,590,276 B2 | 11/2013 | Kryger et al. |
| 8,636,196 B2 | 1/2014 | Hill et al. |
| 8,941,023 B2 | 1/2015 | Holste et al. |
| 9,168,576 B2 | 10/2015 | Unan |
| 10,189,064 B2 | 1/2019 | Takata et al. |
| 2001/0018839 A1 | 9/2001 | Miller |
| 2007/0245789 A1 | 10/2007 | Zepp et al. |
| 2007/0294955 A1 | 12/2007 | Sportel |
| 2009/0021019 A1 | 1/2009 | Thomsen |
| 2009/0113968 A1* | 5/2009 | Pawelski ................ B21B 37/68 72/14.1 |
| 2009/0165518 A1 | 7/2009 | Booth |
| 2009/0188207 A1 | 7/2009 | Gordin et al. |
| 2009/0320542 A1 | 12/2009 | Kephart et al. |
| 2010/0095508 A1 | 4/2010 | Wahlen et al. |
| 2011/0179623 A1 | 7/2011 | Smith et al. |
| 2012/0029294 A1 | 2/2012 | Smith |
| 2012/0273556 A1 | 11/2012 | Unan et al. |
| 2013/0074564 A1 | 3/2013 | Smith et al. |
| 2014/0220371 A1 | 8/2014 | Smith et al. |
| 2015/0273550 A1 | 10/2015 | Takata et al. |
| 2016/0107213 A1 | 4/2016 | Smith et al. |
| 2018/0133769 A1 | 5/2018 | Smith et al. |
| 2019/0063101 A1 | 2/2019 | Smith et al. |
| 2019/0119344 A1 | 4/2019 | Takata et al. |

FOREIGN PATENT DOCUMENTS

| | | |
|---|---|---|
| CN | 1091062 A | 8/1994 |
| CN | 2848445 | 12/2006 |
| CN | 201613273 | 10/2010 |
| CN | 203343212 | 12/2013 |
| CN | ZL201580028200.0 | 11/2022 |
| DE | 1075530 B | 2/1960 |
| EP | 0004538 A1 | 10/1979 |
| EP | 0013870 | 8/1980 |
| EP | 1544376 A2 | 6/2005 |
| GB | 1041159 A | 9/1966 |
| GB | 1075548 A | 7/1967 |
| IN | 412771 | 11/2022 |
| JP | 427145 | 3/1967 |
| JP | S4210073 Y1 | 6/1967 |
| JP | 4431455 | 12/1969 |
| JP | S5956934 A | 4/1984 |
| JP | H01278911 | 11/1989 |
| JP | 58-70918 B2 | 3/2016 |
| KR | 10-2336823 B1 | 12/2021 |
| KR | 10-2409065 B1 | 6/2022 |
| KR | 10-2535480 B1 | 6/2022 |
| MX | 377431 A | 11/2020 |
| MX | 402694 A | 5/2023 |
| MY | 189290 A | 2/2022 |
| VN | 31398 | 2/2022 |
| WO | 2013043920 | 3/2013 |
| WO | 2015148756 | 10/2015 |
| ZA | 201606842 | 9/2018 |

OTHER PUBLICATIONS

EPO; Application No. 15767860.8; Summon to Attend Oral Proceedings dated May 6, 2021, 7 pages.
Intellectual Property India; Application No. 201647036213; First Office Action dated Sep. 16, 2020, 6 pages.
KPO; KR Application No. 10-2016-7030231; Rejection mailed Feb. 10, 2021, 9 pages.
KPO; KR Application No. 10-2016-7030231; Notice of Decision to Grant mailed Oct. 7, 2021, 3 pages.
KPO; KR Application No. 10-2021-7013763; First Office Action dated Aug. 25, 2021, 5 pages.
IMPI; MX/a/2016/012710; Notice of Allowance dated Sep. 30, 2020, 3 pages.
MyIPO; MY Application No. PI 2016703549; Examination and Search Report of Aug. 31, 2021, 3 pages.
Intellectual Property Office of Vietnam; Application No. 1-2016-04135; First Office Action of Oct. 30, 2020, 4 pages.
Intellectual Property Office of Vietnam; Application No. 1-2016-04135; Notice of Allowance dated Sep. 28, 2021, 2 pages.
Human Translation of JP 58-070918. Translated Apr. 2020, 14 pages. (Year 1983).

(56) References Cited

OTHER PUBLICATIONS

USPTO, "U.S. Appl. No. 15/851,472 Non-Final Office Action mailed Jun. 17, 2020", 7 pages.
IP Australia, "Au Application Serial No. 2019202930 Examination Report mailed Apr. 29, 2020", 3 pages.
IP Australia, "Au Application Serial No. 2019202930 Examination Report mailed Jul. 15, 2020", 5 pages.
CNIPA, "Cn AppIn Serial No. 201580028200.0 Decision on Rejection mailed Jul. 17, 2020", English and Chinese Translations , 23 pages.
CNIPA, "CN Appln Serial No. 201811092830.6 Office Action mailed Apr. 2, 2020", English and Chinese Translations , 16 pages.
IMPI, "MX Appln Serial No. MX/a/2016/012710 Office Action mailed Mar. 17, 2020", English and Mexican Translations , 7 pages.
CNIPA, "CN Application No. 201580028200.0 Third Office Action mailed Sep. 19, 2019", English and Chinese translations, 21 pages.
CNIPA, "CN Application No. 201811092830.6 Office Action mailed Oct. 28, 2019", English and Chinese translations, 15 pages.
EPO, "EP Application Serial No. 15767860.8 Examination Report mailed Nov. 22, 2019", 3 pages.
"How to lay out sprial-formed Welded tapered cylinders" by A.A. Pfeifer; Product Engineering; Apr. 15, 1963, Apr. 15, 1963, pp. 88-90.
USPTO, "U.S. Appl. No. 13/623,817 Final Office Action mailed Dec. 10, 2014", 11 pages.
USPTO, "U.S. Appl. No. 13/623,817 Non-Final Office Action mailed Apr. 8, 2015", 12 pages.
USPTO, "U.S. Appl. No. 13/623,817 Non-Final Office Action mailed Jul. 18, 2014", 15 pages.
USPTO, "U.S. Appl. No. 13/623,817 Notice of Allowance mailed Sep. 25, 2015", 9 pages.
USPTO, "U.S. Appl. No. 14/228,481 Notice of Allowance mailed Feb. 1, 2018", 15 pages.
USPTO, "U.S. Appl. No. 14/228,481 Notice of Allowance mailed Oct. 12, 2018", 9 pages.
USPTO, "U.S. Appl. No. 14/247,856 Notice of Allowance mailed Jun. 27, 2016", 9 pages.
USPTO, "U.S. Appl. No. 14/978,175 Non-Final Office Action mailed Mar. 9, 2018", 15 pages.
USPTO, "U.S. Appl. No. 14/978,175 Notice of Allowance mailed Oct. 22, 2018", 5 pages.
USPTO, "U.S. Appl. No. 14/978,175 Notice of Allowance mailed Nov. 8, 2017", 10 pages.
USPTO, "U.S. Appl. No. 15/276,042 Non-Final Office Action mailed Sep. 25, 2017", 9 pages.
USPTO, "U.S. Appl. No. 15/276,042 Notice of Allowance mailed Apr. 27, 2018", 5 pages.
USPTO "U.S. Appl. No. 12/693,369 Final Office Action mailed Aug. 2, 2013", 10 pages.
USPTO, "U.S. Appl. No. 12/693,369 Non-Final Office Action mailed Jul. 13, 2012", 10 pages.
USPTO, "U.S. Appl. No. 12/693,369 Notice of Allowance mailed Dec. 26, 2013", 8 pages.
USPTO, "U.S. Appl. No. 12/693,369, Non-Final Office Action mailed Nov. 7, 2012", 7 pages.
USPTO, "U.S. Appl. No. 14/228,481, Final Office Action mailed Nov. 3, 2016", 14 pages.
USPTO, "U.S. Appl. No. 14/228,481, Non-Final Office Action mailed May 18, 2016", 16 pages.
USPTO, "U.S. Appl. No. 14/247,856 Non-Final Office Action mailed Mar. 28, 2016", 10 pages.
USPTO, "U.S. Appl. No. 14/228,481 Non-Final Office Action mailed Aug. 31, 2017", 15 pages.
USPTO, "U.S. Appl. No. 14/978,175 Non-Final Office Action mailed Jan. 27, 2017", 15 pages.
USPTO, "U.S. Appl. No. 14/978,175, Notice of Allowance mailed May 17, 2017", 5 pages.
AUSPAT, "AU Application No. 2012312351 First Office Action mailed Aug. 8, 2016", 2 pages.
IP AUS, "AU Application No. 2017200527 Examination Report mailed Feb. 5, 2018", 3 pages.
IP Australia, "Au Application Serial No. 2015236028, Examination Report mailed Aug. 10, 2018", 3 pages.
CIPO, "CA Application No. 2,849,300 Examination Report mailed May 11, 2018", 3 pages.
CIPO, "CA Application No. 2,849,300 Examiners Report mailed Mar. 18, 2019", 4 pages.
China Patent Office, "CN Application No. 201280056927.6 Decision on Rejection mailed Jun. 4, 2018", English and Chinese , 19 pages.
CIPO, "CN Application No. 201280056927.6 Office Action mailed May 18, 2017", English and Chinese Translations , 15 pages.
CIPO, "CN Application No. 201280056927.6 Office Action mailed Nov. 6, 2017", English and Chinese translations , 16 Pages.
CIPO, "CN Application No. 201280056927.6 Office Action mailed Dec. 3, 2015", English and Chinese translations , 21 pages.
CIPO, "CN Application No. 201580028200.0 First Office Action mailed Jul. 24, 2018", English and Chinese Translations , 25 pages.
EPO, "EP Application No. 12833030.5 Examination Report mailed Oct. 30, 2017", 7 pages.
EPO, "EP Application Serial No. 12833030.5, EP Supplemental Search Report dated Feb. 12, 2016", 7 pages.
EPO, "EP Application Serial No. 15767860.8 Supplemental Search Report mailed Nov. 7, 2017", 8 pages.
IPO, "IN Application No. 2359/CHENP/2014 First Examination Report mailed Feb. 25, 2019", 7 pages.
International Searchingauthority, "International Application Serial No. PCT/US12056414, Preliminary Report on Patenability mailed Apr. 3, 2014", 6 pages.
ISA, "International Application Serial No. PCT/US15/22648, Search Report and Written Opinion mailed Aug. 12, 2015", 12 pages.
JPO, "JP Application No. 2014-531976 Office Action mailed Aug. 16, 2016", Japanese Translations and English Translations , 6 pages.
JPO, "JP Application No. 2016-242956 First Office Action mailed Jan. 23, 2018", English and Japanese translation , 5 pages.
KIPO, "KR Application Serial No. 10-2014-7008301 Office Action mailed Aug. 24, 2018", English and Korean translations. , 11 pages.
IMPI, "MX Application No. MX/a/2014/003314 Notice of Allowance mailed Jul. 25, 2016", 1 page.
International Searchingauthority, "PCT Application No. PCT/US12/56414 International Search Report and Written Opinion mailed Dec. 14, 2012", 7 pages.
WIPO, "PCT Application No. PCT/US15/22648 International Preliminary Report on Patentability mailed Oct. 13, 2016", 9 pages.
IP Australia, "AU Application Serial No. 2018203517 Examination Report mailed Jun. 18, 2019", 2 pages.
KIPO, "KR Application Serial No. 10-2019-7008024 Office Action mailed May 20, 2019", English and Korean translations , 5 pages.
CNIPA, "CN Application No. 201280056927.6 Notification of ReExamination mailed May 20, 2019", English and Chinese Translations , 14 pages.
CNIPA, "CN Application No. 201580028200.0 Second Office Action mailed Apr. 15, 2019", English and Chinese Translations , 28 pages.
Google Dictionary Definition of "skew" retrieved from Google.com Oct. 13, 2021 (1 page).
Machine Translation of JPS5870918, translated Apr. 2020 (Year: 1983) (14 pages).—Examiner Mar. 4, 2021.
European Patent Office, "European Search Report," issued in related European Patent Application No. EP 19190631.2, dated Sep. 6, 2019 (5 pages).
IP Australia, "Examination Report No. 3," issued in related Australian Patent Application No. 2019202930, dated Sep. 14, 2020 (5 Pages).
Ip Australia, "Examination Report No. 4," issued in related Australian Patent Application No. 2019202930, dated Mar. 5, 2021 (3 pages).
IP Australia, "Examination Report No. 1," issued in related Australian Patent Application No. 2021212066, dated Oct. 12, 2022 (3 Pages).
European Patent Office, "Extended EP Search Report," issued in related European Patent Application No. 22155081.7, dated Aug. 25, 2022. (8 pages).

(56) References Cited

OTHER PUBLICATIONS

Intellectual Property India, "1st Examination Report," issued in related Indian Patent Application No. 202148026370, dated Oct. 18, 2022 (5 pages).
Korean Intellectual Property Office, "Notification of Provisional Rejection," issued in related Korean Patent Application No. 10-2022-7019406, dated Aug. 9, 2022. (5 pages).
Korean Intellectual Property Office, "Notification of Decision to Grant," issued in related Korean Patent Application No. 10-2022-7019406, dated Feb. 20, 2023, including English translation (7 pages).
Mexican Institute of the Industrial Property "1st Substantive Examination," issued in related Mexican Patent Application No. MX/a/2020/012355, dated Oct. 14, 2022, including English translation. (6 pages).
Mexican Institute of the Industrial Property, "Notice of Allowance," issued in related Mexican Patent Application No. MX/a/2020/012355, dated Jan. 27, 2023, (3 pages).
Intellectual Property Corporation of Malaysia, "Preliminary Examination—Clear Formalities Report," issued in related Malaysian Patent Application No. P2016703549, dated Feb. 2, 2022 (4 pages).
European Patent Office, "Examination Report," issued in related European Patent Application No. 22155081.7, dated Nov. 29, 2023 (4 pages).
European Patent Office, "Intention to Grant," issued in related European Patent Application No. 12833030.5 dated Apr. 10, 2019 (47 pages).
China National Intellectual Property Administration, "Decision on Rejection," issued in related Chinese Patent Application No. CN 201580028200.0, dated Jun. 1, 2020, including English Translation (23 pages).
Korean Intellectual Property Office, "Notification of Reason for Refusal," issued in related Korean Patent Application No. KR 10-2014-7008301, dated Aug. 24, 2018, including English translation (11 pages).
Canadian Intellectual Property Office, "Notice of Allowance," issued in related Canadian Patent Application No. 2,849,300, dated Nov. 15, 2019 (1 page).
Canadian Intellectual Property Office, "Notice of Allowance," issued in related Canadian Patent Application No. 3,049,376, dated Mar. 9, 2021 (1 page).
Australian Government, IP Australia, "Notice of Acceptance," issued in related Australian Patent Application No. 2017200527, dated Apr. 9, 2018 (3 pages).
Australian Government, IP Australia, "Certificate of Grant," issued in related Australian Patent Application No. 2017200527, dated Aug. 2, 2018 (1 page).
Japanese Patent Office, "Decision for Patent," issued in related Japanese Patent Application No. 2016-242956, dated Jul. 23, 2018, including English translation (2 pages).
European Patent Officed, "Examination Report," issued in related European Patent Application No. 12833030.5, dated Oct. 30, 2017 (7 pages).
Mexican Institute of Industrial Property, "Office Action," issued in related Mexican Patent Application No. MX MX/a/2014/003314, dated Apr. 27, 2016, (2 pages).
Australian Government, IP Australia, "Notice of Acceptance," in related Australian Patent Application No. 2012312351, dated Oct. 14, 2016 (2 pages).
Australian Government, IP Australia, "Certificate of Grant," issued in related Australian Patent Application No. 2012312351, dated Feb. 9, 2017 (1 page).
Japanese Patent Office, "Decision for Patent," issued in related Japanese Patent Application No. 2014-531976, dated Nov. 10, 2016, including English translation (2 pages).
Canadian Intellectual Property Office, "Examination Search Report," issued in related Canadian Patent Application No. 3,049,376, Oct. 6, 2020 (4 pages).
National Intellectual Property Administration, PRC, "Third Office Action," issued in related Japanese Patent Application No. 201811092830.6, dated Sep. 21, 2020, including English translation (11 pages).
National Intellectual Property Administration, PRC, "Notice to Grant Patent," issued in related Chinese Patent Application No. 201811092830.6, dated Mar. 19, 2021, including English translation (6 pages).
National Intellectual Property Administration, PRC, "First Office Action," issued in related Chinese Patent Application No. 201911152400.3, dated Nov. 4, 2020, including English translation (7 pages).
National Intellectual Property Administration, PRC, "Second Office Action," issued in related Chinese Patent Application No. 201911152400.3, dated Jul. 21, 2021, including English translation (8 pages).
National Intellectual Property Administration, PRC, "Third Office Action," issued in related Chinese Patent Application No. 201911152400.3, Jan. 26, 2022, including English translation (7 pages).
National Intellectual Property Administration, PRC, "Notification to Grant Patent," issued in related Chinese Patent Application No. 201911152400.3, dated Oct. 10, 2022, including English translation (6 pages).
Patents Registry the Hong Kong Special Administrative Region, "Certificate of Grant," issued in related Hong Kong Patent Application No. 42020015198.3, dated Sep. 20, 2012 (3 pages).
European Patent Office, "Extended Search Report," issued in related European Patent Application No. 21199834.9, dated Mar. 2, 2022 (5 pages).
European Patent Office, "Office Action," Issued in related European Patent Appolication No. 21199834.9, dated Nov. 24, 2023 (3 pages).
Australian Government, IP Australia, "Notice of Acceptance," issued in related Australian Patent Application No. 2018203517, dated Feb. 13, 2020 (3 pages).
Australian Government, IP Australia, "Certificate of Grant," issued in related Australian Patent Application No. 2018203517, dated Jun. 11, 2020 (2 pages).
Korean Intellectual Property Office, "Notice of Decision to Grant," issued in related Korean Patent Applicaiton No. 10-2019-7008024, dated Sep. 26, 2019, including English translation (3 pages).
IP Australia, "Examination Report No. 1," issued in related Australian Patent Application No. 2020200768, dated Feb. 24, 2021, (4 pages).
IP Australia, "Examination Report No. 2," issued in related Australian Patent Application No. 2020200768, dated Dec. 1, 2021, (2 pages).
IP Australia, "Notice of Acceptance," issued in related Australian Patent Application No. 2020200768, dated Feb. 23, 2022, (3 pages).
National Institute of Industrial Property, First Office Action, issued in related Brazilian Patent Application No. 112014006605-1, dated Jan. 6, 2020 (4 pages).
National Institute of Industrial Property, Notice of Allowance as Published, issued in related Brazilian Patent Application No. 112014006605-1, dated Dec. 28, 2021 (2 pages).
China National Intellectual Property Administration, "Notification of Re-examination," issued in related Chinese Patent Application No. 201280056927.6, dated May 20, 2019 (14 pages).
Canadian Intellectual Property Office, "Notice of Allowance," issued in related Canadian Patent Application No. CA 2,944,178, dated Dec. 9, 2022 (1 page).
Canadian Intellectual Property Office, "Examiner's Report," issued in related Canadian Patent Application No. CA 2,944,178, dated Jan. 18, 2022 (9 pages).
Canadian Intellectual Property Office, "Examiner's Report," issued in related Canadian Patent Application No. CA 2,944,178, dated May 3, 2023 (7 pages).
Korean Intellectual Property Office, "Decision to Grant," issued in related Korean Patent Application No. 10-2021-7013763, dated Mar. 10, 2022, including English translation, (3 pages).
Companies and Intellectual Property Commission, "Notice of Acceptance," issued in related South African Patent Application No. 2014/02257, dated Jul. 10, 2015, (3 pages).
United States Patent and Trademark Office, "Notice of Allowability," issued in related U.S. Appl. No. 13/623,817, dated Mar. 2, 2016 (6 pages).

(56) References Cited

OTHER PUBLICATIONS

United States Patent Office, "Corrected Notice of Allowability," issued in related U.S. Appl. No. 14/978,175, dated Jul. 21, 2017 (4 pages).

United States Patent Office, Notice of Allowance, issued in related U.S. Appl. No. 14/978,175, dated Sep. 25, 2017 (7 pages).

United States Patent Office, Corrected Notice of Allowability, issued in related U.S. Appl. No. 14/978,175, dated Nov. 9, 2018 (6 pages).

United States Patent and Trademark Office, "Notice of Allowance," issued in related U.S. Appl. No. 15/851,472, dated Dec. 16, 2020 (19 pages).

United States Patent and Trademark Office, "Non-Final Office Action," issued in related U.S. Appl. No. 17/199,019, dated Mar. 30, 2022 (9 -pages).

United States Patent and Trademark Office, "Notice of Allowance," issued in related U.S. Appl. No. 17/199,019, dated Oct. 5, 2022 (21 pages).

United States Patent and Trademark Office, "Restriction Requirement," issued in related U.S. Appl. No. 14/228,481, dated Feb. 5, 2016 (9 pages).

United States Patent and Trademark Office, "Non-Final Office Action," issued in related U.S. Appl. No. 16/208,831, dated Oct. 3, 2019 (26 pages).

United States Patent and Trademark Office, "Final Office Action," issued in related U.S. Appl. No. 16/208,831, dated Apr. 9, 2020 (14 pages).

United States Patent and Trademark Office, "Non-Final Office Action," issued in related U.S. Appl. No. 16/208,831, dated Mar. 10, 2021 (19 pages).

United States Patent and Trademark Office, "Notice of Allowance," issued in related U.S. Appl. No. 16/208,831, dated Oct. 27, 2021 (9 pages).

United States Patent and Trademark Office, "Notice of Allowance," issued in related U.S. Appl. No. 16/208,831, dated Feb. 25, 2022 (13 pages).

IP Australia, "Notice of Acceptance," issued in related Australian Patent Application No. 2021212066 dated Oct. 20, 2023, (3 pages).

\* cited by examiner

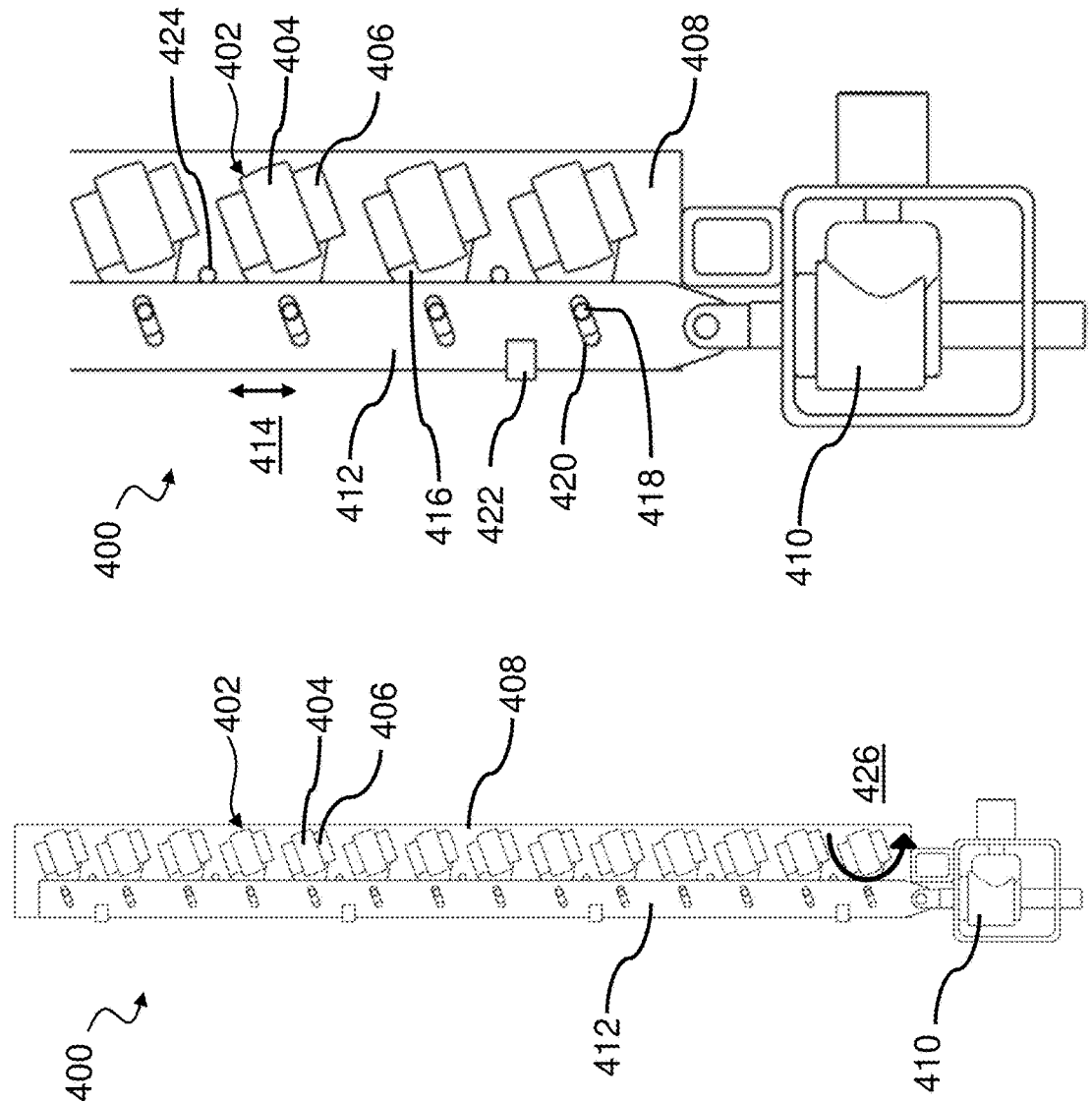

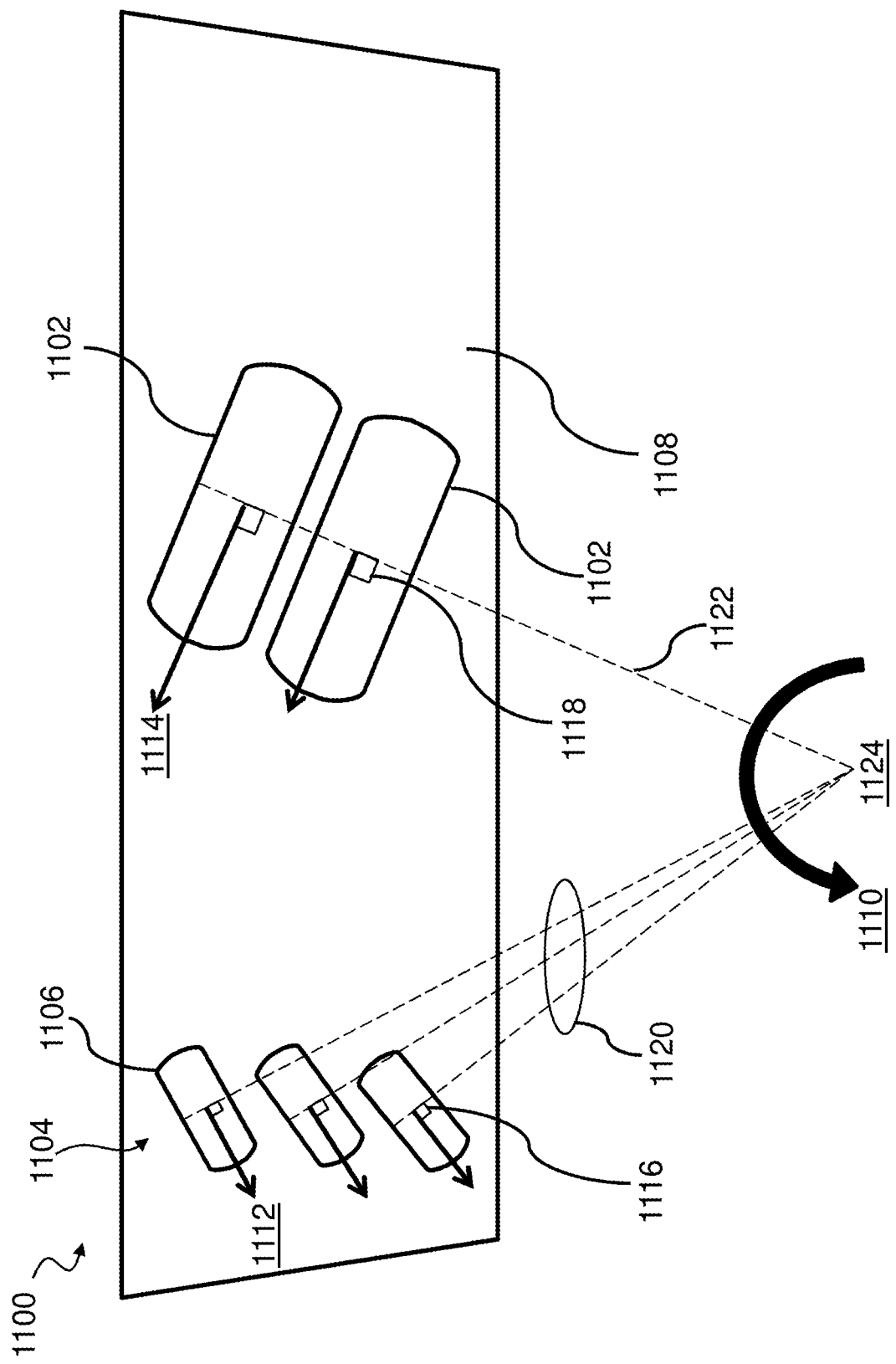

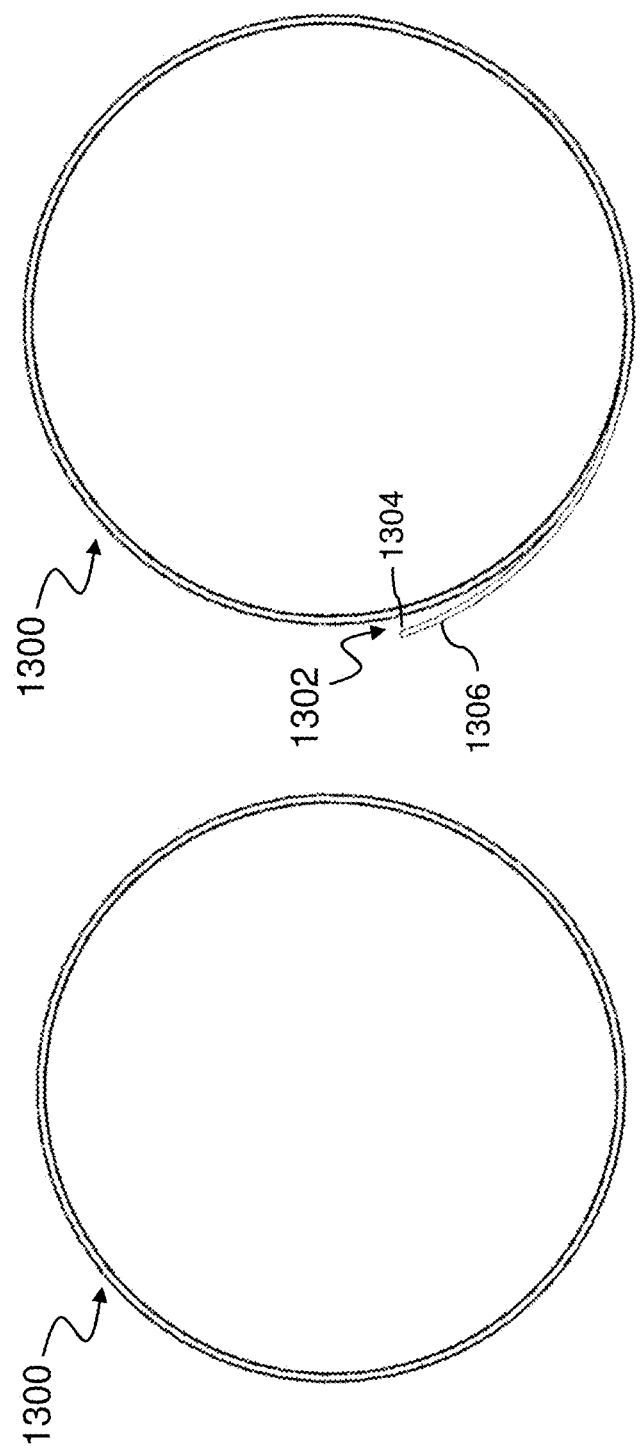

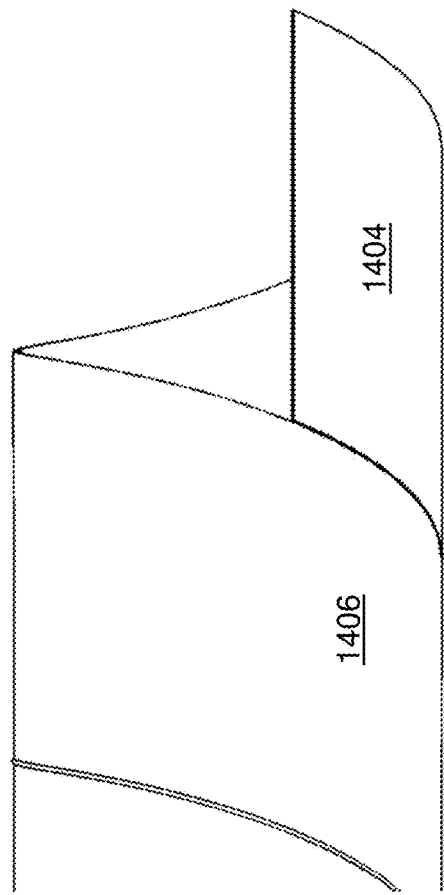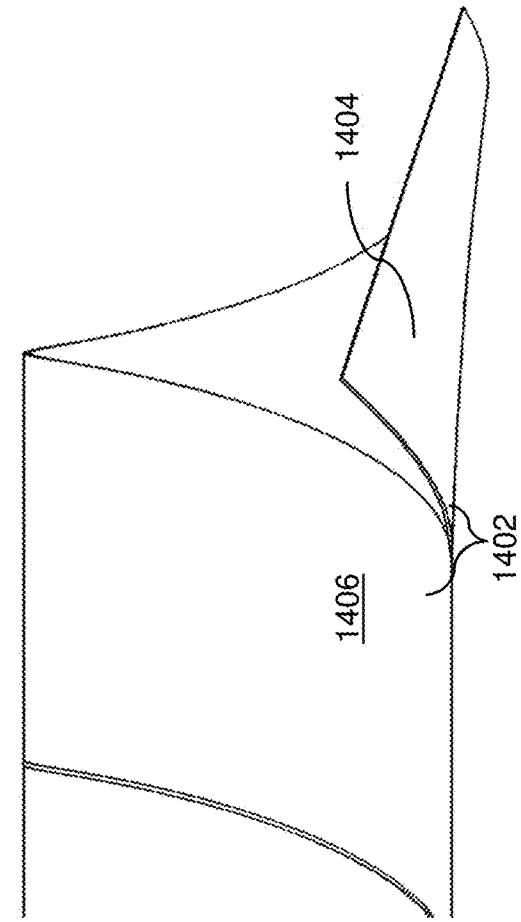

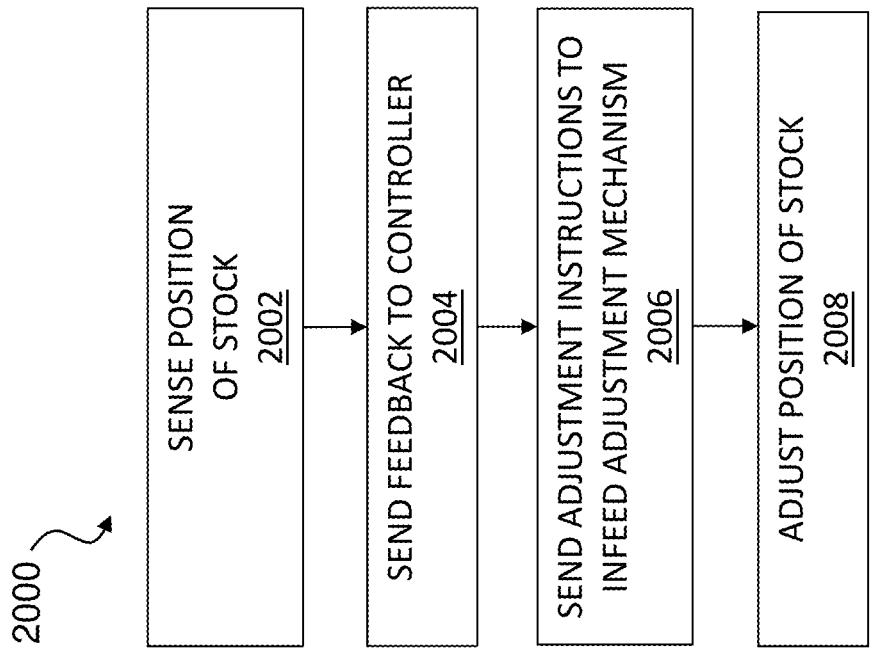
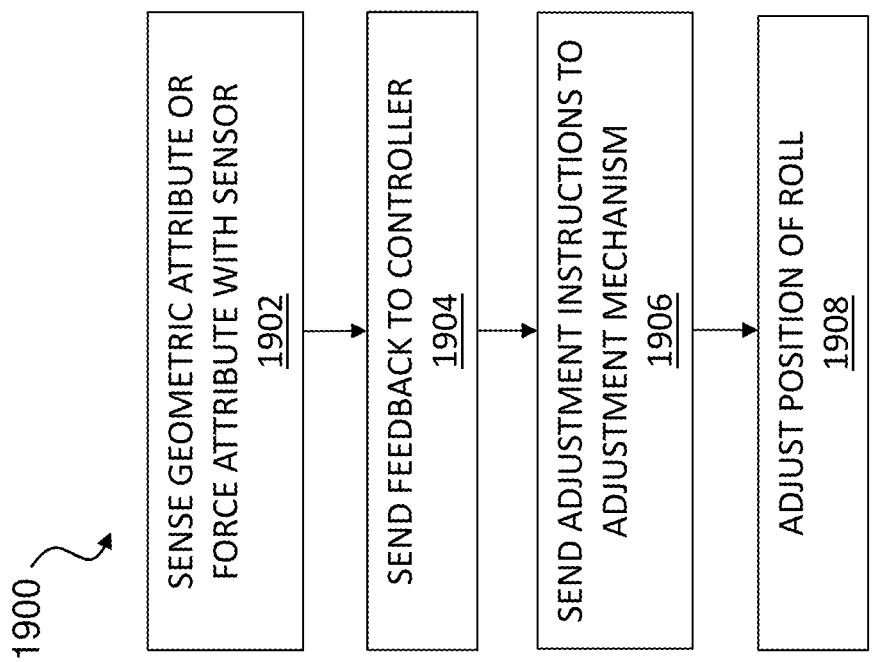

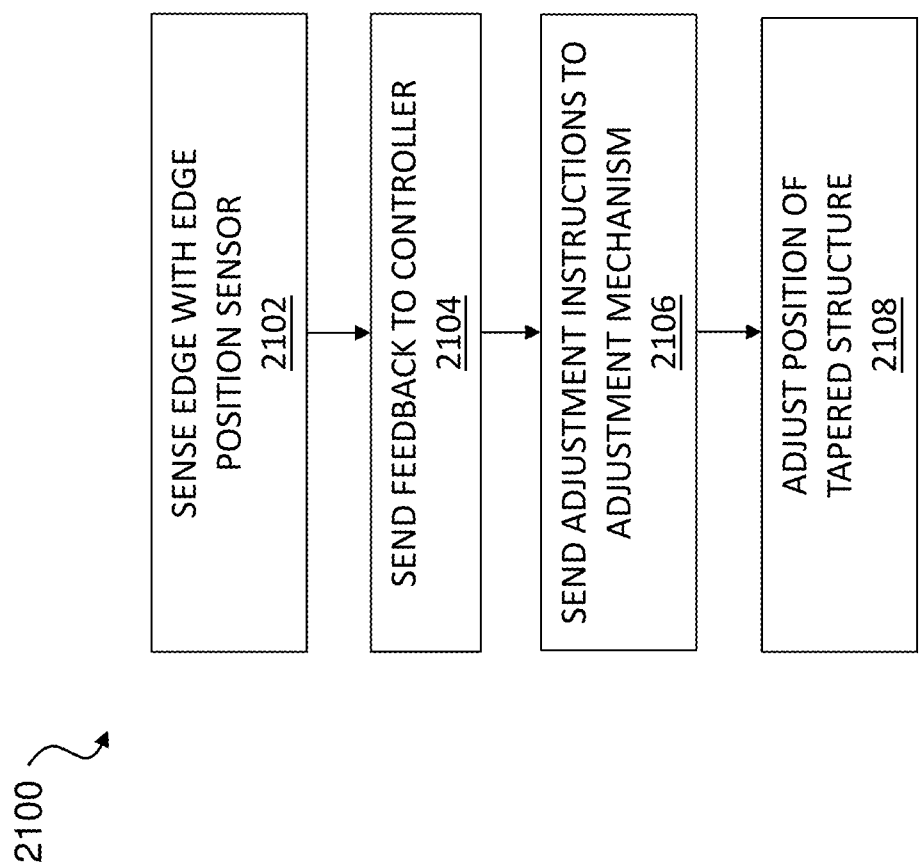

CONTROL SYSTEM AND METHOD FOR TAPERED STRUCTURE CONSTRUCTION

CROSS-REFERENCE TO RELATED APPLICATIONS

This application is a continuation of U.S. patent application Ser. No. 16/208,831, filed Dec. 4, 2018, which is a continuation of U.S. patent application Ser. No. 14/228,481, filed Mar. 28, 2014 (now issued as U.S. Pat. No. 10,189,064), the entire contents of which are hereby incorporated herein by reference. This application is related to U.S. patent application Ser. No. 13/623,817, filed on Sep. 20, 2012 (now issued as U.S. Pat. No. 9,302,303), which claims priority to U.S. Provisional Application No. 61/537,013, filed on Sep. 20, 2011, each of which is hereby incorporated by reference in its entirety.

This application is also related to U.S. patent application Ser. No. 12/693,369, filed on Jan. 25, 2010 (now issued as U.S. Pat. No. 8,720,153), which is hereby incorporated by reference in its entirety.

STATEMENT REGARDING FEDERALLY SPONSORED RESEARCH OR DEVELOPMENT

This invention was made with government support under contract DE-SC0006380 awarded by the Department of Energy. The government has certain rights in the invention.

This invention was made with government support under the NSF SBIR PI award 1248182 awarded by the National Science Foundation. The government has certain rights in the invention.

TECHNICAL FIELD

This document generally relates to a control system for tapered structure construction, and a method for controlling the machinery for constructing tapered structures.

BACKGROUND

Various techniques and devices exist that can produce tapered structures, such as cones or frusto-conical structures. One general approach to constructing tapered structures involves bending or otherwise deforming metal stock in desired ways, then joining the stock either to itself at certain points, or joining the stock to other structures at certain points. The control systems for such techniques do not facilitate the substantially continuous and accurate construction of a tapered structure, for example, a tapered structure for use as a wind turbine tower.

Spiral welding machines exist that form continuous diameter tubes, for example, for pipes and the like. These machines may include control systems where an operator adjusts a parameter of the spiral welding machine based on a measurement of the tube diameter. However, the manufacture of a tapered structure has additional difficult-to-control degrees of freedom and hence there exists a need for a control system and method for tapered structure construction where the machinery for forming tapered structures is adjusted continuously and automatically to create a substantially error free tapered structure.

SUMMARY

In general, in one aspect, a control system for forming a tapered structure includes a sensor providing feedback for a machine for forming a tapered structure. The machine for forming a tapered structure may include at least three rolls including at least one bend roll and at least two guide rolls. The guide rolls may include rollette banks having a plurality of rollettes. The machine for forming a tapered structure may also include an adjustment mechanism configured to position at least one of the rolls, where a diameter of the tapered structure being formed is controlled by relative positions of the rolls. The machine for forming a tapered structure may also include a joining element configured to join edges of a stock of material together as the stock of material is rolled through the rolls to form the tapered structure. The control system may also include a controller configured to receive feedback from the sensor and to send a control signal based on the feedback to the adjustment mechanism for positioning at least one of the rolls.

In general, in another aspect, a control system for forming a tapered structure includes a sensor providing feedback for a machine for forming a tapered structure. The machine for forming a tapered structure may include at least three rolls including at least one bend roll and at least two guide rolls. The guide rolls may include rollette banks having a plurality of rollettes. The machine for forming a tapered structure may also include an infeed adjustment mechanism configured to position a stock of material as it is fed into the rolls, where the stock of material forms the tapered structure as it is rolled through the rolls. The machine for forming a tapered structure may also include a joining element configured to join edges of the stock of material together as the stock of material is rolled through the rolls to form the tapered structure. The control system may also include a controller configured to receive feedback from the sensor and to send a control signal based on the feedback to the infeed adjustment mechanism for positioning the stock of material as it is fed into or through the machine for forming a tapered structure.

In general, in yet another aspect, a control system for forming a tapered structure includes an edge position sensor configured to provide feedback including a position of an edge of a stock of material to be formed into a tapered structure in a machine for forming a tapered structure. The machine for forming a tapered structure may include a rolling assembly having a plurality of rolls, a joining element configured to join edges of the stock of material together as the stock of material is rolled through the rolling assembly to form the tapered structure, a runout system configured to support the tapered structure after the edges are joined, and an adjustment mechanism configured to position the tapered structure relative to the rolling assembly. The control system may also include a controller configured to receive feedback from the edge position sensor and to send a control signal based on the feedback to the adjustment mechanism to achieve a desired relative movement between portions of the tapered structure.

In general, in another aspect, a control system for forming a tapered structure includes a model for use in a machine for forming a tapered structure. The machine for forming a tapered structure may include at least three rolls including at least one bend roll and at least two guide rolls. The guide rolls may include rollette banks having a plurality of rollettes. The machine for forming a tapered structure may also include an adjustment mechanism configured to position at least one of the rolls, where a diameter of the tapered structure being formed is controlled by relative positions of the rolls. The machine for forming a tapered structure may further include a joining element configured to join edges of a stock of material together as the stock of material is rolled through the rolls to form the tapered structure. The model may include relative positions of the rolls for desired tapered structure diameters. The control system may also include a computer configured to implement the model, and a controller configured to receive instructions based on the model and to send a control signal based on the instructions to the adjustment mechanism for positioning at least one of the rolls.

In general, in yet another aspect, a control system for forming a tapered structure includes a model for use in a machine for forming a tapered structure. The machine for forming a tapered structure may include at least three rolls including at least one bend roll and at least two guide rolls. The guide rolls may include rollette banks having a plurality of rollettes. The machine for forming a tapered structure may also include an infeed adjustment mechanism configured to position a stock of material as it is fed into the rolls, where the stock of material forms the tapered structure as it is rolled through the rolls. The machine for forming a tapered structure may further include a joining element configured to join edges of the stock of material together as the stock of material is rolled through the rolls to form the tapered structure. The model may include relative positions of the stock of material as it is fed into or through the machine for forming a tapered structure. The control system may also include a computer configured to implement the model, and a controller configured to receive instructions based on the model and to send a control signal based on the instructions to the infeed adjustment mechanism for positioning the stock of material.

In general, in another aspect, a method for controlling the formation of a tapered structure includes sensing with a sensor, on a system for forming a tapered structure, at least one of a geometric attribute of the tapered structure being formed and a force attribute of the tapered structure being formed. The system for forming a tapered structure may include at least three rolls including at least one bend roll and at least two guide rolls. The guide rolls may include rollette banks having a plurality of rollettes. The system for forming a tapered structure may also include an adjustment mechanism configured to position at least one of the rolls, where a diameter of the tapered structure being formed is controlled by relative positions of the rolls. The system for forming a tapered structure may further include a joining element configured to join edges of a stock of material together as the stock of material is rolled through the rolls to form the tapered structure. The method may also include: sending feedback from the sensor to a controller, where the feedback is based on at least one of the geometric attribute and the force attribute; sending adjustment instructions from the controller to the adjustment mechanism, where the adjustment instructions are based on the feedback; and adjusting a position of at least one of the rolls with the adjustment mechanism based on the adjustment instructions.

In general, in yet another aspect, a method for controlling the formation of a tapered structure includes sensing with a sensor, on a system for forming a tapered structure, a position of a stock of material for forming into the tapered structure. The system for forming a tapered structure may include at least three rolls including at least one bend roll and at least two guide rolls. The guide rolls may include rollette banks having a plurality of rollettes. The system for forming a tapered structure may also include an infeed adjustment mechanism configured to position the stock of material as it is fed into at least one of the rolls, where the stock of material forms the tapered structure as it is rolled through the rolls. The system for forming a tapered structure may further include a joining element configured to join edges of the stock of material together as the stock of material is rolled through the rolls to form the tapered structure. The method may also include: sending feedback from the sensor to a controller, where the feedback is based on the position of the stock of material; sending adjustment instructions from the controller to the infeed adjustment mechanism, where the adjustment instructions are based on the feedback; and adjusting with the adjustment mechanism the position of the stock of material as it is fed into or through the system for forming a tapered structure based on the adjustment instructions.

In general, in another aspect, a method for controlling the formation of a tapered structure includes sensing with an edge position sensor, on a system for forming a tapered structure, a position of an edge of a stock of material to be formed into the tapered structure. The system for forming a tapered structure includes: a rolling assembly having a plurality of rolls; a joining element configured to join edges of the stock of material together as the stock of material is rolled through the rolling assembly to form the tapered structure; a runout system configured to support the tapered structure after the edges are joined; and an adjustment mechanism configured to position the tapered structure relative to the rolling assembly. The method may also include: sending feedback from the edge position sensor to a controller, where the feedback is based on the position of the edge of the stock of material; sending adjustment instructions from the controller to the adjustment mechanism, where the adjustment instructions are based on the feedback; and adjusting a position of the tapered structure relative to the rolling assembly using the adjustment mechanism based on the adjustment instructions.

In general, in yet another aspect, a method for controlling the formation of a tapered structure includes: driving a stock of material with an infeed system; feeding the stock of material through a rolling assembly having at least three rolls including at least one bend roll and at least two guide rolls, where the guide rolls include rollette banks having a plurality of rollettes; joining edges of the stock of material together as the stock of material is rolled through the rolling assembly to form a tapered structure; guiding the stock of material out of the rolling assembly with a runout system; and sensing, with a sensor, sensor data including at least one of (i) a geometric attribute of the tapered structure being formed, (ii) a force attribute of the tapered structure being formed, (iii) a position of the stock of material, (iv) an inconsistency in a weld gap in the stock of material, (v) a planar alignment error in the stock of material, and (vi) an angular alignment error in the stock of material. The method may also include: sending feedback from the sensor to a controller, where the feedback is based on the sensor data; sending adjustment instructions from the controller to an adjustment mechanism, where the adjustment instructions are based on the feedback; and adjusting a position of the stock of material using the adjustment mechanism based on the adjustment instructions.

Other implementations of any of the foregoing aspects can be expressed in various forms, including methods, systems, apparatuses, devices, computer program products, products by processes, or other forms. Other advantages will be apparent from the following figures and description.

BRIEF DESCRIPTION OF THE DRAWINGS

The foregoing and other objects, features, and advantages of the systems and methods described herein will be apparent from the following description of particular embodiments thereof, as illustrated in the accompanying drawings. The drawings are not necessarily to scale, emphasis instead being placed upon illustrating the principles of the systems and methods described herein.

FIGS. 4A and 4B are top views of a rollette bank.

FIGS. 11A and 11B are schematic depictions of sheet steering.

FIGS. 13A and 13B are schematic illustrations of an out-of-plane gap error.

FIGS. 14A and 14B are schematic illustrations of a tangency alignment error.

FIG. 19 is a flow chart of a method for controlling the formation of a tapered structure.

FIG. 20 is a flow chart of a method for controlling the formation of a tapered structure.

FIG. 21 is a flow chart of a method for controlling the formation of a tapered structure.

Figure 1:
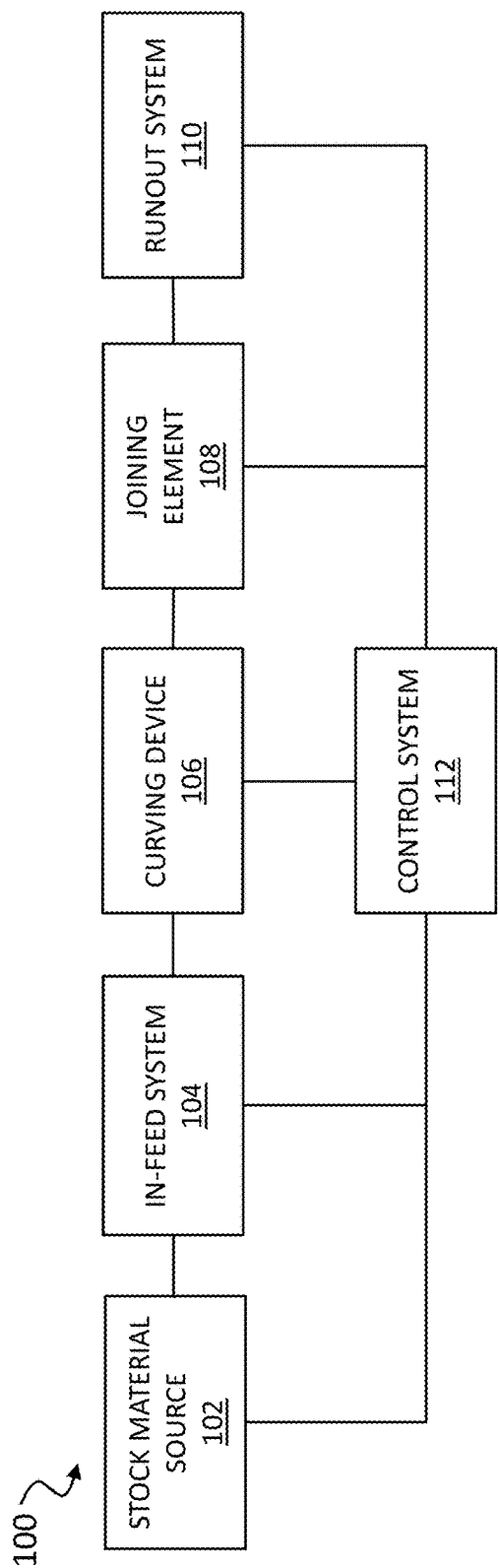
FIG. 1 is a block diagram of a construction system for forming tapered structures.

Like references numbers refer to like structures.

DETAILED DESCRIPTION

The embodiments will now be described more fully hereinafter with reference to the accompanying figures in which preferred embodiments are shown. The system and methods described herein may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The word "about," "approximately," and the like, when accompanying a numerical value, is to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "top," "bottom," "above," "below," "first," "second," "up," "down," "left," "right," and the like, are words of convenience and are not to be construed as limiting terms.

It is often desirable to form a tapered structure, such as a conical or frusto-conical structure, from a substantially planar stock without introducing substantial in-plane deformation to the stock. For example, U.S. patent application Ser. No. 12/693,369, entitled "TAPERED SPIRAL WELDED STRUCTURE," discusses some applications of such structures. Additionally, U.S. patent application Ser. No. 13/623,817, entitled "TAPERED STRUCTURE CONSTRUCTION," discusses some construction systems for such structures. Among other things, the techniques described below can be used in conjunction with the systems, devices, and methods described in these applications, both of which are incorporated by reference in their entirety. Additionally, the control systems and methods described herein may be used in addition to, in conjunction with, or in replacement of any controls described in these applications.

FIG. 1 is a block diagram of a construction system. The system 100 includes a stock material source 102 (which may be metal), an infeed system 104, a curving device 106, a joining element 108, a runout system 110, and a control system 112. As described more fully herein, the system 100 is operable to construct tapered structures. In one aspect, the control system 112 controls at least one of the stock material source 102, infeed system 104, curving device 106, joining element 108, and runout system 110. However, one skilled in the art will appreciate that in other aspects the control system 112 may control more or less components of the construction system 100, and any combinations thereof. In addition, the components, or combinations thereof, may include individual controls/control systems, where in one aspect the control systems are in communication with one another.

The stock material source 102 may include the raw metal from which a tapered structure is formed. In some implementations, the stock material source 102 can include a collection of planar metal sheets, dimensioned in any of the ways described in U.S. patent application Ser. No. 12/693, 369, a roll of stock material, or the like. The sheets can be constructed and arranged to facilitate easily picking a desired sheet in the manufacturing process. For example, the sheets can be stored in a magazine or other suitable dispenser. As used throughout this disclosure, the "stock," "stock of material," "sheet", and the like, shall refer to the material to be formed into the tapered structure unless explicitly stated otherwise or clear from the text. As discussed above, in some implementations the stock can include a roll of metal or other material. In some implementations the stock comprises pre-cut individual sheets.

The infeed system 104 is operable to transport metal from the stock material source 102 to (and in some implementations, through) the curving device 106. The infeed system 104 can include any such appropriate equipment for transporting a desired sheet according to traditional techniques. Such equipment can include, for example, robotic arms, pistons, servos, screws, actuators, rollers, drivers, electromagnets, or the like, or combinations of any of the foregoing. As described herein, a control system may include an infeed control system that includes controls for feeding the stock material into the curving device 106 in such a manner that a desired tapered structure can be formed.

The curving device 106 is operable to curve the material fed into it, and in one aspect, without imparting any in-plane deformation to the material. Moreover, the curving device 106 can impart a controllable degree of curvature to the material. In an implementation, the curving device includes a plurality of rolls. Rolls as described herein may include, but are not limited to, rollers (including substantially cylindrical rollers, substantially cone-shaped rollers, irregularly-shaped rollers, spherical rollers, or the like), a rollette bank that includes a plurality of rollettes (e.g., smaller rollers, wheels, bearings, spherical rollers, or the like) that collectively approximate the exterior of the corresponding solid structure, or any other element that may be used to bend/roll/manipulate a stock of material into a tapered structure. The curving device 106 may include a triple roll 200 as shown schematically in FIG. 2 (described in more detail below). As used throughout this disclosure, the "curving device," "rolling assembly," "triple roll," and the like, shall refer to any device or component operable to curve the material fed into it (e.g., as described herein), unless otherwise stated or clear from the context.

The joining element 108 is operable to join sheets of in-fed stock to other sheets of in-fed stock (or to themselves, or to other structures). In some implementations, the joining element 108 is a welder that includes one or more weld heads whose position and operation is controllable by a control system. In general, the joining element 108 may include any component or machine for joining the stock by any known means, including welding, adhesives, epoxy, crimps, rivets, bolts, fasteners, complementary geometric features (e.g., pins that mate with holes, teeth that mate with each other, snaps, etc.), and the like. The joining element 108 may be configured to join edges of the stock of material together as the stock of material is rolled through the curving device 106. In some implementations, there may be multiple joining elements and/or multiple steps for joining edges of the stock of material together. For example, for trapezoidal shaped sheets of stock having a pair of long sides and a pair of short sides, the short sides may be joined first (e.g., with other sheets of stock), then the stock deformed, and then the long sides joined.

The runout system 110 is operable to transport material from the curving device 106 and joining element 108 (i.e., the structure taking form or being formed). This may involve supporting, holding, transporting, moving, guiding, manipulating, pushing, pulling, twisting, etc., the structure being formed. The runout system 110 can include any such appropriate equipment according to traditional techniques. Such equipment can include, for example, robotic arms, pistons, servos, screws, actuators, rollers, drivers, electromagnets, subsystems, or the like, or combinations of any of the foregoing. As described herein, a control system may include a runout control system that includes controls for supporting and positioning the tapered structure being formed after the edges of the stock of material are joined.

The control system 112 is operable to control and coordinate the various tasks described herein, including, but not limited to, operating the infeed system 104, operating the curving device 106, operating the joining element 108, and operating the runout system 110. The control system 112 may include computer hardware, software, circuitry, or the like that can collectively generate and deliver control signals to the components and systems described herein to accomplish the desired tasks.

The control systems and methods described herein can generally be used for any of the construction machinery described herein including the machinery and systems described in the references incorporated by reference in their entirety herein. In general, a "control system" may refer to an individual control system for an individual component/piece of machinery, or to a combination of control systems, or to a control system that controls numerous components/pieces of machinery and/or systems.

As discussed herein, it may be desirable to arrange for the stock being fed into system 100 to undergo a purely rotational motion during the infeed process. Specifically, the purely rotational motion may take place as the stock is fed into the curving device 106. The control systems and methods described herein may be designed to achieve this function.

Although the phrase "purely rotational" motion has been used, slight deviations from pure rotation (i.e., slight translations of the stock or peak relative to each other) may be permissible. If the stock undergoes any translational motion with respect to the peak during the infeed process, the resultant structure may deviate from an ideal frusto-conical geometry. In particular, there may be gaps where the stock fails to meet corresponding edges of predecessor portions of stock, the stock may overlap itself, or both. Therefore, a control system as described herein may control the stock of material to prevent translational motion relative to the peak. However, slight translational motion may be acceptable, e.g., if the gap is kept within an acceptable range.

As used in this document, "substantially rotational" motion means purely rotational motion as described above, except for allowing for slight deviations that may be useful later in the manufacturing process, or be acceptable because the structure geometry can still be kept within a desired range/tolerance, or that are small enough to not detrimentally affect cone geometry, buckling strength, fatigue strength, etc. The degree of these permissible deviations, in general, will vary with the dimensions of the desired frusto-conical structure and the manufacturing steps that the deviations accommodate. Also as used in this document, "rotational motion" should be understood to mean either substantially rotational motion or purely rotational motion.

A triple roll will now be described.

Figure 2:
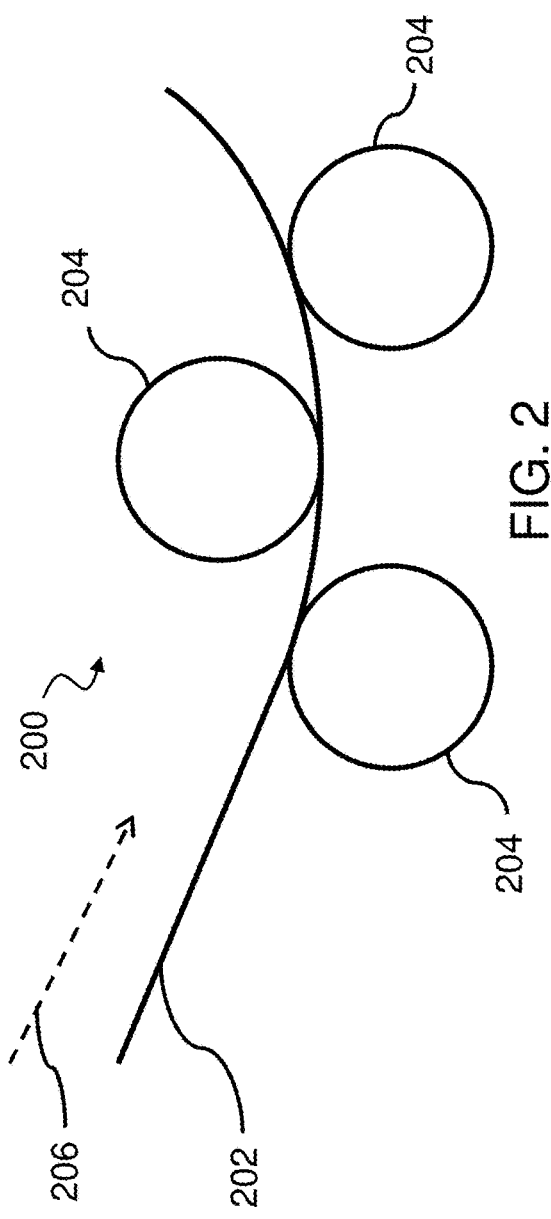
FIG. 2 is a schematic depiction of a triple roll.

FIG. 2 represents a simple schematic of how a basic triple roll 200 may operate. The triple roll 200 may include three substantially cylindrical rollers 204 that are substantially parallel to one another and that are operable to impart a curvature to a stock of material 202 fed through the rollers 204 in the direction of the dashed arrow 206. The triple roll may also or instead include one or more banks of rollettes that are operable to impart a curvature to the stock of material in the same manner as solid rollers 204. The degree of curvature can be controlled by, e.g., dynamically adjusting the relative positions of the rollers 204 or rollette banks, etc.

Figure 3:
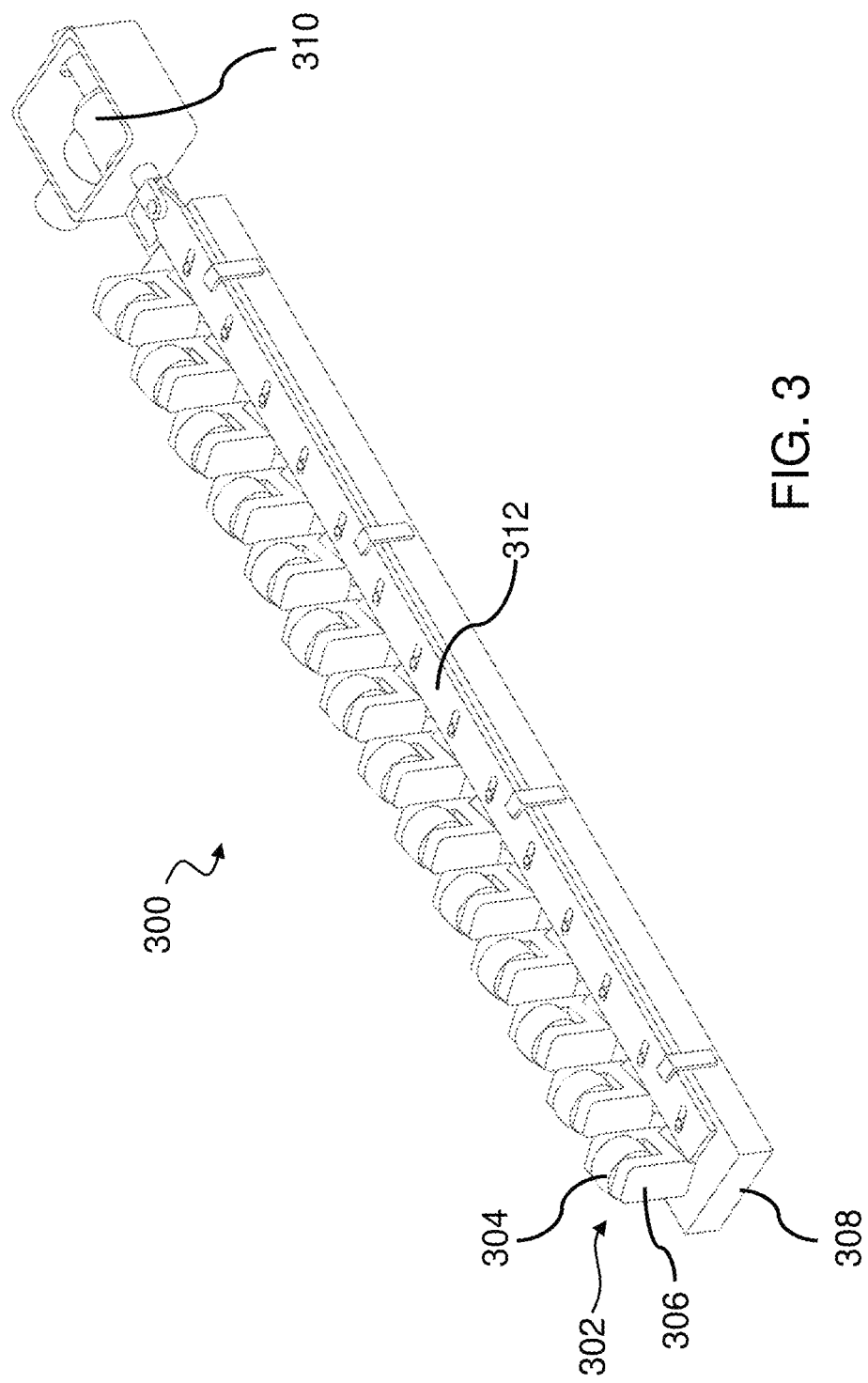
FIG. 3 is an isometric view of a rollette bank.

FIGS. 3, 4A and 4B show an example of a rollette bank with a rollette steering mechanism including cam plate steering. Specifically, FIG. 3 shows an example of a rollette bank 300. As shown in FIG. 3, the rollette bank 300 may include a plurality of rollettes 302. The rollettes 302 may include rollers whose axes of revolution are adjustable with respect to other axes of revolution in a triple roll. The rollettes 302 may be steered using a cam plate steering system as described below. The rollettes 302 may include a roller 304 (e.g., a cylindrical roller, spherical roller, sliding pad, and so forth) and a body 306 or housing that may support/hold the roller 304. The rollette bank 300 may also include a base 308, where the body 306 may interface with the base 308 thereby coupling the rollettes 302 to the rollette bank 300, e.g., in a manner that permits rotation relative to the base 308 of the rollette bank 300. One of ordinary skill will recognize that there are other means for connecting the rollettes 302 to the rollette bank 300.

The rollette bank 300 may also include a rollette steering mechanism. The rollettes 302 may interface with the rollette steering mechanism, where such an interface may be made possible by the body 306 or the base 308 of the rollette bank 300. The steering mechanism may include, without limitation, cams, a four-bar linkage or other linkages, individual steering actuators, and the like. For example, FIG. 3 shows a rollette steering mechanism that includes a steering actuator 310 that drives a steering cam plate 312, which in turn can steer the rollettes 302. The rollette steering mechanism may also or instead include any form of a rollette adjustment mechanism configured to position angles of the rollettes 302 on the rollette bank 300.

FIGS. 4A and 4B show a rollette bank 400 with a rollette steering mechanism. The rollette bank 400 includes rollettes 402 having rollers 404 and a roller housing 406. The rollette bank 400 shown in FIGS. 4A—B also includes a base 408. As best shown in FIG. 4B, the rollette steering mechanism may include a cam plate actuator 410 configured to move a cam plate 412 in at least the directions shown by the arrows 414. The rollettes 402 may be engaged with the cam plate 412 by any means known in the art, including, without limitation, via a rollette arm 416 including a cam mating pin 418 that connects to the cam plate 412 through a corresponding cam slot 420. The cam mating pin 418 may instead be replaced by a roller, cam follower, and the like. The cam slots 420 may be cut into configurations such that when the cam plate 412 is moved, the geometry of the cam slots 420 causes the cam mating pins 418 to move, thereby rotating the rollettes 402. The cam slots 420 in the cam plate 412 may all be the same, or they may be different for each rollette 402. If the rollettes 402 are identical to each other, and the cam slots 420 on the cam plate 412 are the same, then the rollettes 402 will move together and will be at substantially the same angle. If the rollettes 402 are different from each other (i.e., if the angle of the rollette arm 416 relative to the roller axis varies between rollettes 402) and the cam slots 420 in the cam plate 412 are the same, then the rollettes 402 will move together but may be at different angles from each other. If the cam slots 420 in the cam plate 412 are different for one or more rollettes 402, then the movement of the rollettes 402 will have some correspondence (i.e., from the geometry of the cam slot 420) but they won't necessarily move together. For example, the cams could be constructed such that some rollettes don't move at all, while others rotate. A skilled artisan will recognize that many configurations are possible.

The cam plate 412 itself may be actuated relative to the rollettes 402 in order to rotate the rollettes 402. The cam plate 412 may be guided or held in place by any known means, including, without limitation, a cam plate hold down 422 and a cam plate guide 424, or slides, bearings, rollers, pins, linkages, etc. Activating the cam plate actuator 410 may move the cam plate 412 in the direction shown by the arrows 414, which in turn, due to the coupling of the rollette arm 416 and the cam plate 412, rotates the rollettes 402, for example, along the axis of rotation 426 indicated in FIG. 4A. The cam plate 412 may be actuated by any means known to a skilled artisan including, without limitation, electric motors, pneumatics, hydraulics, etc.

A control system for rolling a stock of material and forming a tapered shape with a substantially continuously changing diameter, and the machine components thereof, will now be discussed. As used throughout this disclosure, a structure with a "substantially continuously" changing diameter shall refer generally to a tapered structure such as a cone, truncated cone, or the like. Similarly, as used throughout this disclosure, "substantially continuously" adjusting a diameter (or the like) shall refer to generally creating a tapered structure such as a cone, truncated cone, or the like. As will be recognized by a skilled artisan, a tapered structure may include either an actual peak or a virtual peak. An actual peak is a point at which the diameter eventually decreases to zero. For example, a cone has an actual peak at its apex. For a truncated structure, such as a frusto-conical structure, a "virtual peak" is the point at which the diameter would eventually decrease to zero if the structure were not truncated. As used herein, the word "peak" includes both actual peaks and virtual peaks.

Figure 5A:
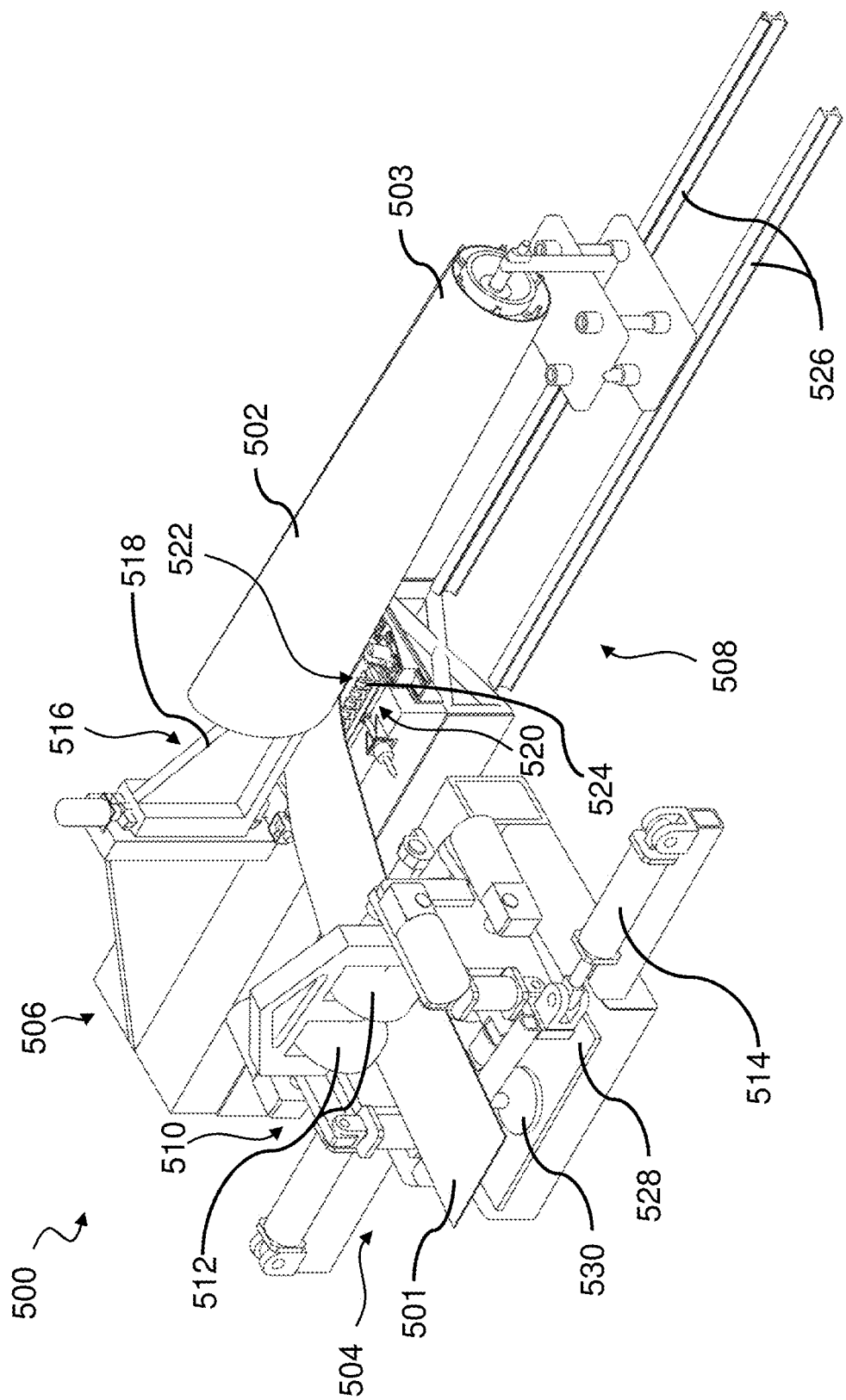
FIG. 5A is an isometric view of a construction system for forming tapered structures.
Figure 5B:
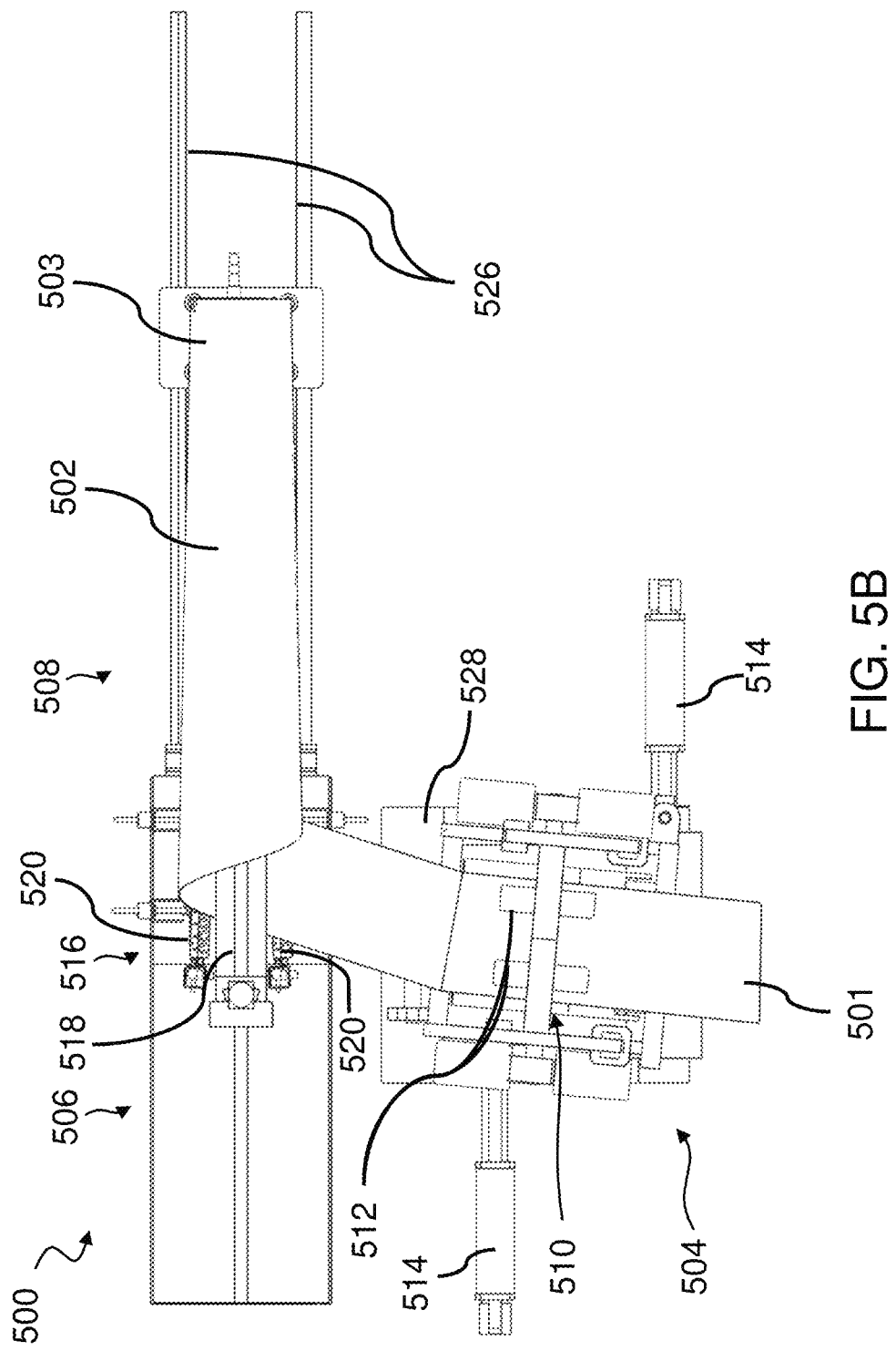
FIG. 5B is a top view of a construction system for forming tapered structures.
Figure 6:
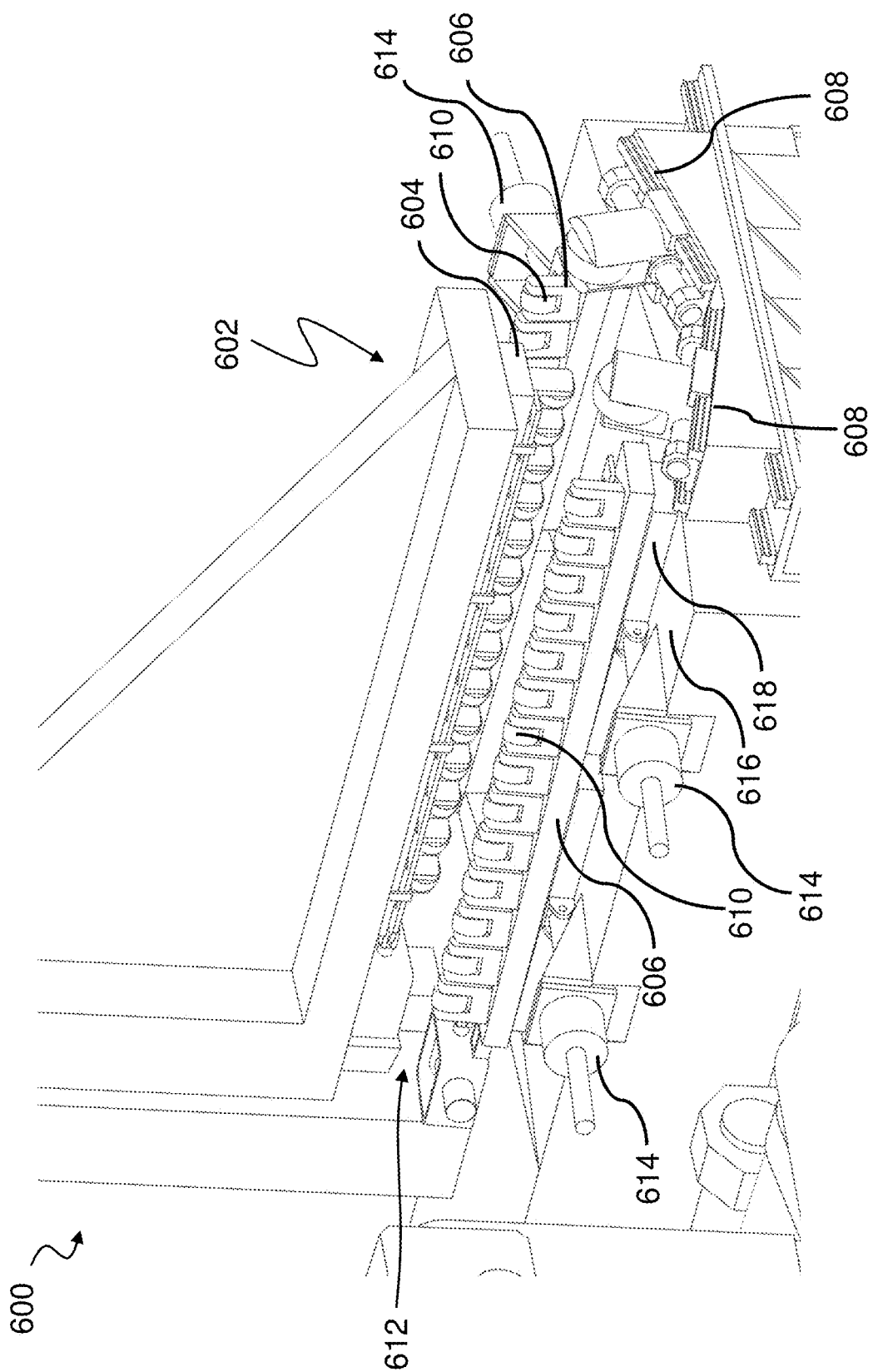
FIG. 6 is an isometric view of a curving device.

An implementation of a machine for forming a tapered structure is shown in FIGS. 5A-6, which will now be described in more detail.

FIGS. 5A and 5B depict a construction system 500 for forming tapered structures according to an embodiment, where FIG. 5A shows an isometric view of the system 500 and FIG. 5B shows a top view of the system 500. Specifically, FIGS. 5A—B show a construction system 500 for forming tapered structures from a stock of material 501, such as a truncated cone 502 that can be used as a wind turbine tower. As used throughout this disclosure, the "tapered structure," "cone," truncated cone," and the like, shall refer to a structure formed by the devices, systems, and methods described herein. The system 500 may include a plurality of subsystems, including a stock material source (not shown), an infeed system 504, a curving device 506, a joining element (not shown), a control system (not shown), and a runout system 508.

The infeed system 504 is operable to perform a function including, without limitation, feeding, transporting, guiding, forcing, positioning, etc., a stock of material 501 to (and in some implementations, through) the curving device 506. As shown in FIGS. 5A—B, the infeed system 504 may include a drive roll 510 with infeed rollers 512, and an infeed actuator 514. The components of the infeed system 504 may be supported by an infeed base 528, which may include a frame, which may be positionable. The drive roll 510 may feed the stock of material 501 into the curving device 506, and the drive roll 510 may steer the stock of material 501 into the curving device 506. The steering of the stock of material 501 may be enabled by the infeed actuator 514, which is able to adjust at least one of a position of the stock of material 501, a position of the drive roll 510, a position of the infeed rollers 512, a position of the infeed base 528, and a position of the entire infeed system 504. The infeed actuator 514 may also be able to adjust an angle of the aforementioned components in an implementation. Other configurations of the infeed system 504 are possible, including embodiments with a singular drive roll (which may not be a "roll" at all), implementations with more or less actuators, or implementations with other means for providing an adjustment mechanism for the infeed system 504. In general, the infeed system 504 may include a drive roll adjustment mechanism configured to adjust a position and angle of the drive roll 510. A combination of an infeed adjustment mechanism and the drive roll adjustment mechanism may position the stock of material 501. In an implementation, the infeed system 504 may impart no constraint on the stock's motion, and the stock of material 501 need not rotate with respect to any other point in the infeed system 504.

The curving device 506 may generally include a triple roll 516 with a top roll 518 and two bottom rolls 520. The rolls of the triple roll 516 may generally include a rollette bank 522 that includes a plurality of rollettes 524, which may be in the form of rollers.

The infeed system 504 and the curving device 506 may be supported separately on their own frames, or may be on a single frame which allows the infeed system 504 and the curving device 506 to move together (not shown). Alternatively, either or both of the infeed system 504 and the curving device 506 may be stationary. Also, either or both of the infeed system 504 and the curving device 506 may be able to move independently. The supports (and/or a single frame in an embodiment not shown) may be adjustable with many degrees of freedom, e.g., in a direction parallel to the central axis of the truncated cone 502 (the x-direction, i.e., toward and away from the peak 503 of the cone 502), in a direction normal to the central axis of the cone 502 (the y-direction, i.e., toward and away from the tracks 526 of the runout system 508), up and down, (the z-direction) and rotating about the x, y and z axes, and to rotate the frame about various axes (e.g., if adjusting roll position rather than run-out position for gap control). The movement of these components may be accomplished through means known by skilled artisans, including, without limitation, hydraulic pistons, pneumatic pistons, servos, screws, actuators, rack and pinion systems, cable and pulley systems, cams, electromagnetic drives, robotic arms, rollers, drivers, or the like, or combinations of any of the foregoing or other devices capable of imparting the desired motion. Moreover, although not described herein, subsystems of the components shown may be mobile (e.g., certain arms and supports may be positionable in any manner a skilled artisan might envision).

FIG. 6 is a close up view of an implementation of the curving device 600, i.e., the roll forming system. As described herein, in some embodiments, the curving device 600 includes a triple roll 602. The triple roll 602 may include a top roll 604, and two bottom rolls 606 (or conversely a bottom roll and two top rolls—not shown). The top roll 604 may be articulated vertically—either manually, or under the direction of a curving device control system or other control system. Articulating the top roll 604 can be useful, for example, to engage the stock of material, or to control the amount of curvature imparted to the stock of material as it passes through the triple roll 602. The bottom rolls 606 can also or instead be articulated, for example, along sloped surfaces 608 that support the bottom rolls 606, along another sloped surface or path, or along a curved surface or path. Moving the bottom rolls 606 may be done for the same or similar purposes as moving the top roll 604, e.g., to make it easier to start feeding the stock of material, and to control the diameter of the tapered structure being formed. In general, any of the rolls of the triple roll 602 can be articulated, and any controllable change in the relative position of the rolls can be used to impart corresponding amounts of curvature to the stock of material.

In some implementations, and as described above, the triple roll 602 includes a plurality of individual rollettes 610 arranged in banks. In general, banks of rollettes may allow the direction of travel of the stock of material through the triple roll to be at an angle other than perpendicular to the axis of bending as the stock of material is rolled. For example, in a triple roll with three solid rolls, the direction of the axis of bending is basically parallel to the axes of the rolls, and the stock of material is compelled by the rotation of the rolls to move in a direction perpendicular to this direction, so that the stock of material is forced to roll back on itself. Very large side forces may be needed to change this orientation. For the purposes of continuously rolling a cylindrical or tapered shape, the stock of material should be able to be fed in to the triple roll at an angle that may allow the stock of material to be formed into a helix, where rollette banks may be utilized to allow this to occur.

Figure 23:
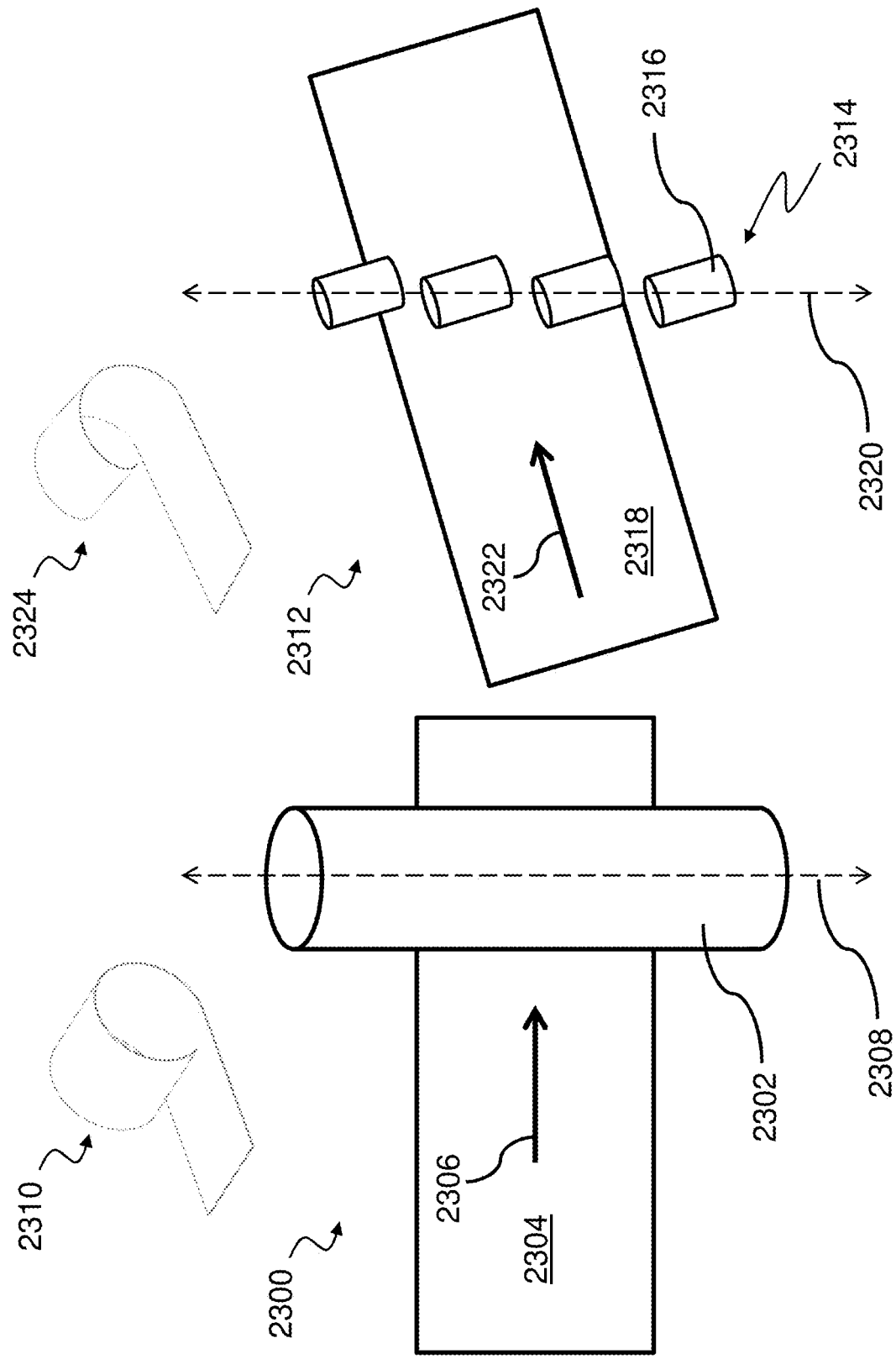
FIG. 23 is a schematic depiction of a solid roller and a rollette bank.

When banks of rollettes are used, the bend axis may still be substantially parallel to the orientations of the rollette banks, while the stock of material may be compelled to move in the direction of the rollettes. To demonstrate a difference between the use of a solid roller and the use of rollette banks, FIG. 23 shows a first configuration 2300 with a solid roller 2302. In the first configuration 2300, the stock of material 2304 is fed through the solid roller 2302 in a first feed direction 2306, which may be normal to the bend axis 2308. This may produce a first bent roll 2310 similar to that shown above the first configuration 2300 (i.e., the direction of the bend axis 2308 is substantially parallel to the axis of the solid roller 2302, and the stock of material 2304 is compelled by the rotation of the solid roller 2302 to move in a direction perpendicular to this direction, so that the stock of material 2304 is forced to roll back on itself as shown by the first bent roll 2310). Alternatively, as shown in the second configuration 2312, the angle of the rollettes 2316 on the rollette bank 2314 may be independent of the position of the rollette bank 2314. The stock of material 2318 thus may be fed at any angle relative to the bend axis 2320 as long as the direction of the stock of material 2318 is generally along the rolling direction of the rollettes 2316. Thus, it may be advantageous to have the heading of the rollettes 2316 be independent of the direction of the bend axis 2320—the system may have the same bend axis 2320, but rotate the rollettes 2316 such that the in-feed angle can change, which changes the angle of the helix formed by rolling the stock of material 2318. For example, the stock of material 2318 may be fed along the second feed direction 2322. This may produce a second bent roll 2324 similar to that shown above the second configuration 2312, i.e., more of a helix shape than the first bent roll 2310 produced by the first configuration 2300. This may be advantageous for substantially continuous rolling and welding processes, where the stock of material is fed into the rolling machine at a desired angle, and is formed into what is more or less a helix (i.e., it may be a helix for cylinders, and may be a helix-like structure for cones) that is then joined into a solid shape.

In various implementations, the rolls can be individually driven, driven collectively, or not driven at all. Similarly, in various implementations, the rollettes can be individually driven, driven collectively, or not driven at all. The rollettes may also be individually steered, steered collectively, or not steered at all. In an embodiment, the banks are substantially parallel. In another embodiment, the banks need not be parallel.

Turning back to FIG. 6, in an implementation, the bottom rolls 606 are lower rollette banks, which are movable in both translation and angle. That is, the bottom rolls 606 can be moved closer and farther apart while remaining parallel, and their relative angle can also be changed, so that, for example, the distance between corresponding rollettes 610 of each rollette bank near the throat 612 of the curving device 600 can be greater than the distance between corresponding rollettes 610 farthest away from the throat 612. This may assist the system in forming tapered structures, and in controlling the diameter and taper of the structure being formed. In the implementation shown in FIG. 6, the actuation of the rollette banks is done with four screw jacks 614 driven by electric motors, with the rollette banks sliding on a low-friction surface 616 between sets of guides 618. A skilled artisan will recognize that other means for moving the rollette banks are possible, for example, the rollette banks could also be guided by profile rails, other types of rails, slides, bushings, linkages, and the like, and the actuation could be done with ball screws, screw jacks, rack and pinions, belts, pistons, and the like.

The relationship between the roll position (e.g., rollette bank position) and the resulting radius of curvature of the tapered structure being formed will now be discussed.

Figure 7:
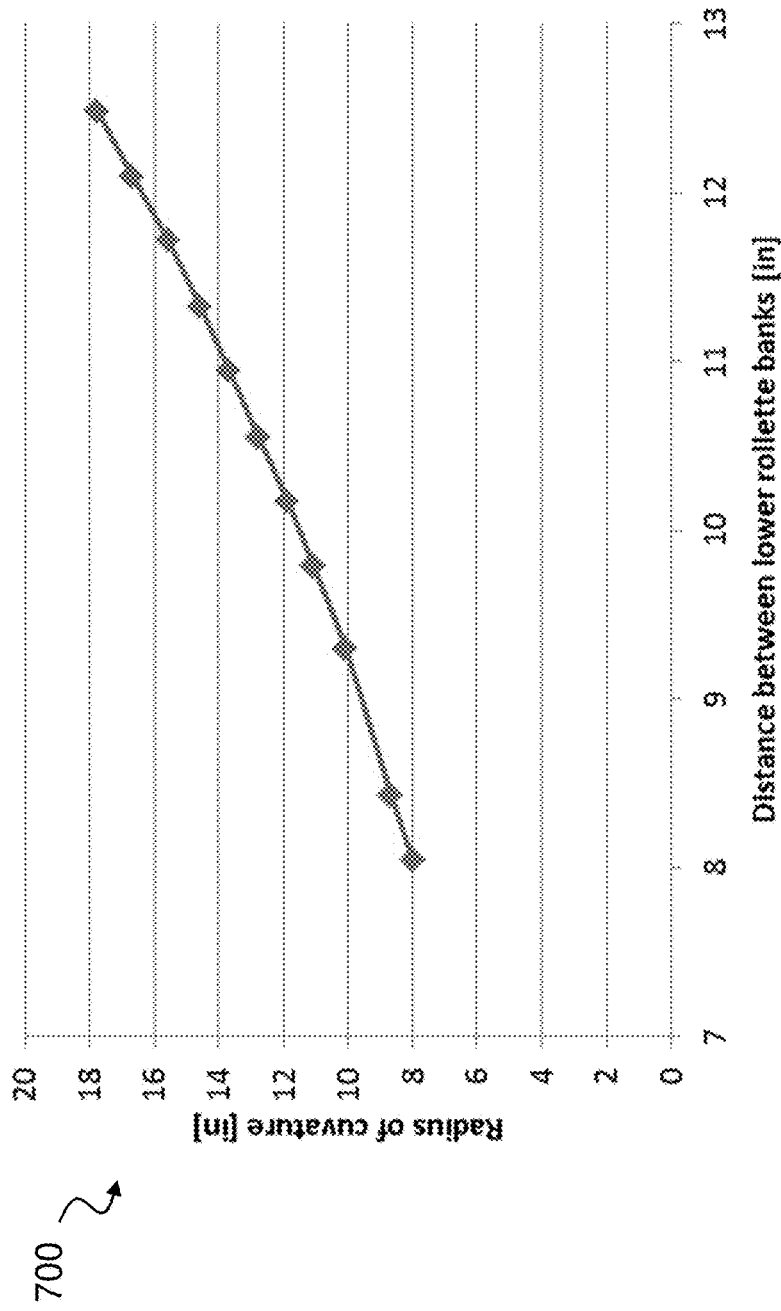
FIG. 7 is a plot showing a relationship between rollette bank positions and a resulting radius of curvature of a tapered structure being formed.
Figure 8:
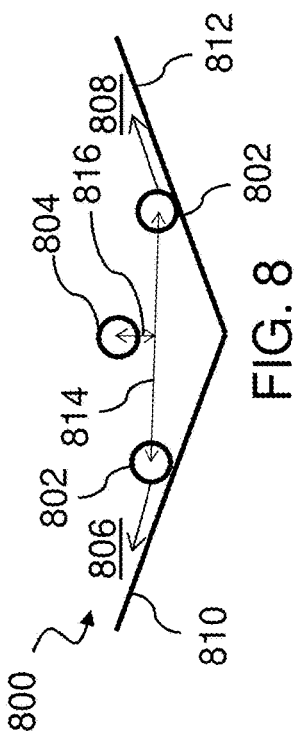
FIG. 8 is a schematic depiction of a triple roll.

FIG. 7 shows an example of model results predicting rolled diameter for a given distance between lower rollette banks, e.g., the bottom rolls 802 of FIG. 8. Specifically, FIG. 7 represents a plot 700 where the stock of material is approximately 0.075" thick steel with an approximate yield strength of 50 ksi. For example, this model 700, likely along with empirical adjustments made based on testing results, could be used as the basis for a control system that continuously controls the diameter of the tapered structure being formed by substantially continuously adjusting the positions of the rollette banks of a triple roll. This control system could be used with or without an additional feed-back system Specifically, FIG. 7 shows a plot 700 that includes example model results for the relationship between the rollette bank positions and the resulting radius of curvature of the tapered structure being formed. The plot 700 includes the distance between the bottom rolls (e.g., lower rollette banks) in a triple roll along the x-axis, where the x-axis includes a distance from 7-13 inches. The plot 700 further includes the radius of curvature of the tapered structure being formed along the y-axis, where the y-axis includes a radius of curvature from 0-20 inches.

FIG. 8 is a diagram that represents the rolls in a triple roll 800, including two bottom rolls 802 and a top roll 804, where the rolls may be rollette banks. The first and second arrows 806, 808 represent the bottom rolls 802 moving away from each other along sloped surfaces 810, 812. The first double arrow 814 represents the distance between the bottom rolls 802. The second double arrow 816 represents the distance between the bottom rolls 802 and the top roll 804.

As stated above, in an implementation, the degree of imparted curvature from the curving device (e.g., the triple roll) may be controlled continuously. To form a conical or frusto-conical structure, for example, the curvature with which a given point on the in-coming stock of material is deformed may vary linearly with the height along the resultant cone's axis at which the given point will lie. Other tapered structures may include other degrees of imparted curvature. FIGS. 7 and 8 show a way in which the rolls or rollette banks of the triple roll can be adjusted to control the tapered structure diameter. In an implementation, the top roll 804 is fixed in place, and the two bottom rolls 802 are moved (i.e., along the direction shown by the arrows 806, 808), in order to change the relative distance between the three rolls. The bottom rolls 802 may be moved along sloped surfaces 810, 812, as shown in FIG. 8. As shown in the figures, the distance between either one of the bottom rolls 802 and the top roll 804 may change as the distance between the bottom rolls 802 changes, because the bottom rolls 802 are on sloped surfaces 810, 812 and the top roll 804 may be fixed. That is, in this example, the larger the distance between the bottom rolls 802, the smaller the distance between each bottom roll 802 and the top roll 804. In one aspect (e.g., for a shallow slope), when the bottom rolls 802 are moved farther apart from each other, the stock of material is given a lower amount of curvature as it passes between the rollers, and when the bottom rolls 802 are moved closer together the stock of material is given more curvature. The sloped surfaces 810, 812 may allow the system to become less sensitive to errors in roll positioning—as the bottom rolls 802 move farther from each other they move closer to the top roll 804, reducing the effect of their movement on the rolled diameter relative to movement along a flat surface. In one aspect, it may also be possible to have a steep enough slope such that moving the bottom rolls 802 away from each other makes the rolled diameter smaller, because with a steep slope the bottom rolls 802 do not get much farther away from each other but do get a lot closer to the top roll 804.

Sheet steering (i.e., steering the stock of material) will now be discussed.

In general, sheet steering may be accomplished using components of the infeed system and/or rolling assembly. In addition to control of the diameter of the tapered structure being formed, the system may also include a control for the infeed angle at which the stock of material is fed into the curving device. This can be accomplished in many ways. In general, at least two degrees of freedom should be present— that is, it typically isn't sufficient to only control the infeed angle (e.g., with a system that can swing an infeed base, such as those in cylindrical spiral mills) without having control of the material position. The implementation illustrated in the figures included herein (see, e.g., FIGS. 5A—B) uses a combination of an actuated drive system and steerable rollettes to achieve the desired infeed motion.

Figure 9:
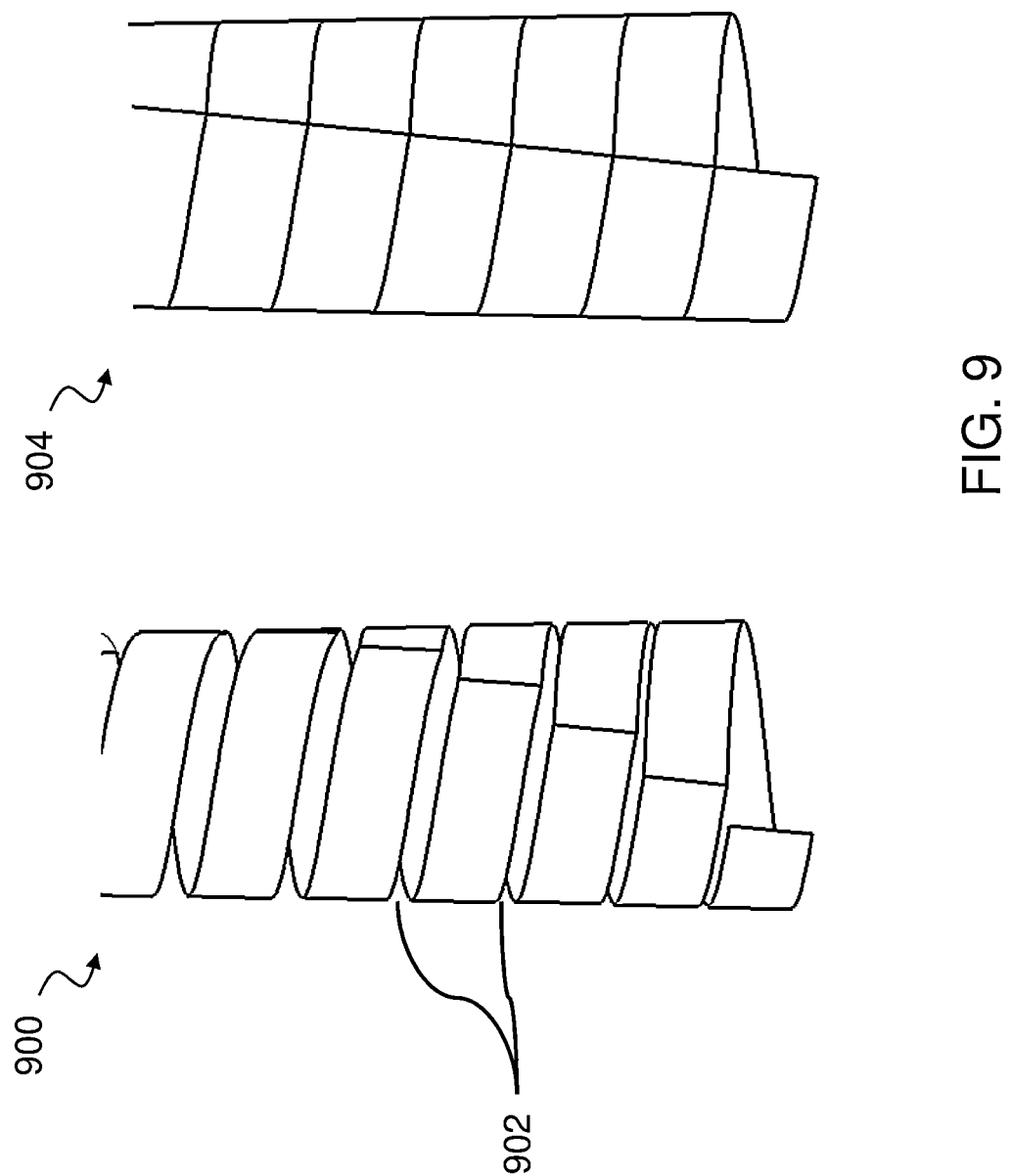
FIG. 9 is a top view of a structure with gap errors and a structure without gap errors.

Sheet steering helps prevent gaps from forming in the tapered structure. An example of gaps in a tapered structure is shown in FIG. 9. Specifically, FIG. 9 shows a tapered structure 900 with gap errors 902, and a tapered structure 904 without gap errors.

Figure 10:
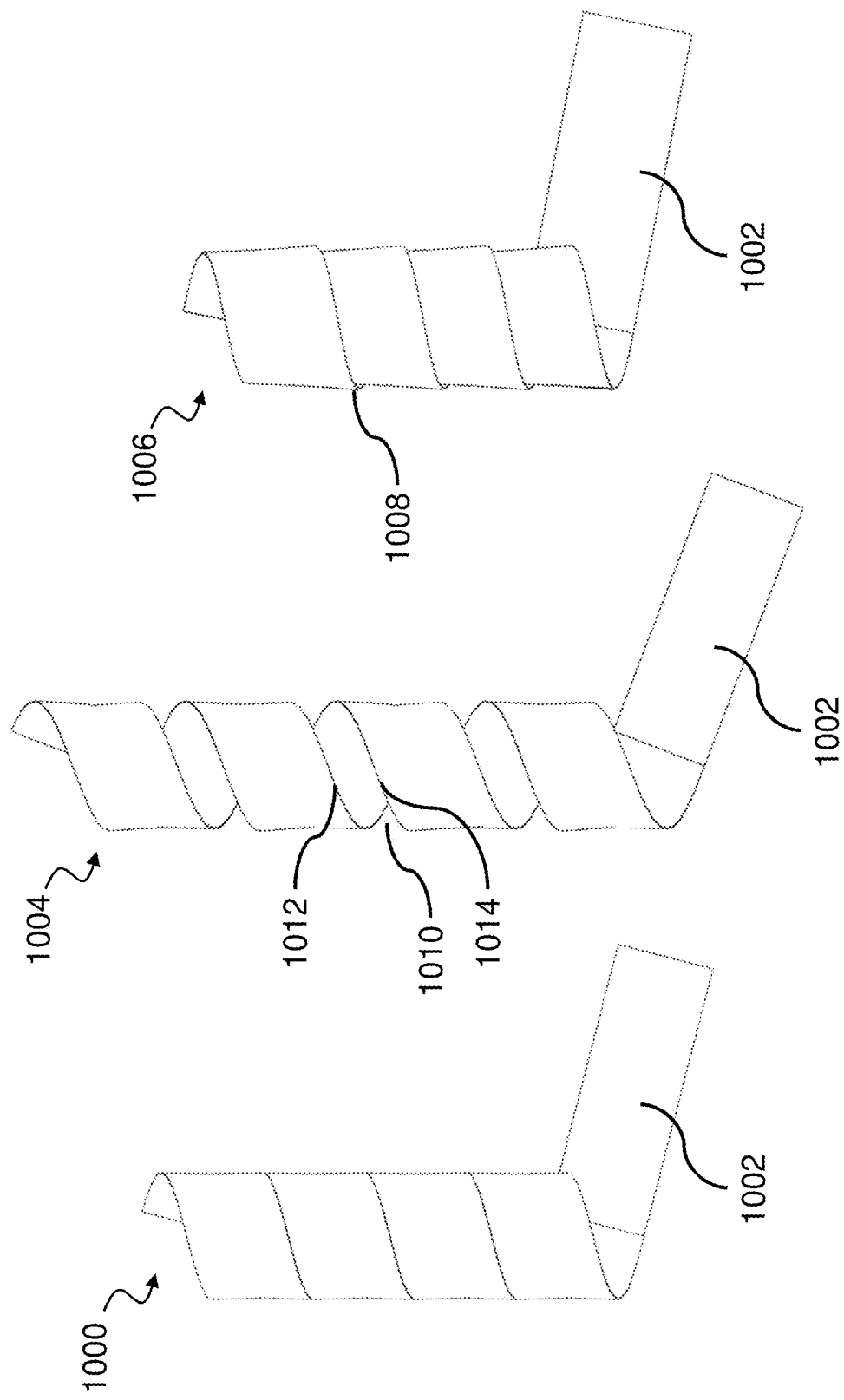
FIG. 10 is a top view of a structure formed by feeding material at different angles.

In general, a piece of stock may be fed into the curving device (e.g., triple roll) at the correct angle and position in order to form the desired tapered structure without gaps or overlaps between turns. As used in this disclosure, a skilled artisan will understand that "without gaps" (or the like) includes the stock having an intentional, controlled gap, e.g., for welding or the like. FIG. 10 shows an example of a tapered structure 1000 formed by feeding the stock of material at different angles. It is noted that FIG. 10 depicts a cylinder but it will be referred to as a tapered structure 1000 because the principles of FIG. 10 hold true for tapered structures as well as cylinders. A cylinder is only used for convenience to clearly illustrate the relationships discussed below (e.g., with a cylinder, a straight sheet has the same infeed angle, whereas for a tapered structure, the infeed angle varies as it's rolled, so the relationships below may not be visible at particular instants using a tapered structure). FIG. 10 shows a tapered structure 1000 where the stock of material 1002 was fed into the curving device at the correct angle, a tapered structure 1004 where the stock of material 1002 was fed into the curving device at too steep of an angle, and a tapered structure 1006 where the stock of material 1002 was fed into the curving device at too shallow of an angle. As shown by the tapered structure 1006 in FIG. 10, a relatively shallow infeed angle may cause a piece of stock 1002 to wrap back on itself more tightly, possibly causing an overlap 1008. As shown by the tapered structure 1004 in FIG. 10, a relatively steep infeed angle may cause the wrapped section of stock 1002 to be farther away, possibly resulting in a gap 1010 between corresponding edges 1012, 1014 of the stock 1002. The correct infeed angle causes the stock 1002 to wrap into the desired shape while maintaining the desired gap for joining edges of the stock (see tapered structure 1000 in FIG. 10). For a tapered structure, this infeed angle may vary as the stock is fed into the curving device. Some of the techniques described herein involve control systems that may vary the infeed angle (and other parameters described herein) such that the edges of the stock lie adjacent to each other, allowing them to be joined (e.g., metal sheets with edges welded together) to form a desired structure 904, 1000, as shown in FIGS. 9 and 10, respectively.

A control system according to one aspect is able to vary the infeed angle by controlling the approach of the stock of material so that the stock is purely rotating (i.e., not translating) with respect to the peak of the tapered structure as the stock is fed into the curving device. This condition is equivalent to having each point on the incoming sheet of stock be at a constant distance from the peak of the tapered structure as the stock is fed into the curving device. However, the peak of the tapered structure itself might be moving relative to other parts of the system, as described more fully below. The purely rotational condition described above concerns only the relative motion of the in-fed stock with respect to the peak's location. That is, both the stock and the peak may also be translating or undergoing more complicated motion with respect to other components of the system. If this condition is met, then even irregularly shaped stock can be joined into a tapered structure.

As discussed above, the infeed system may feed the stock material into the curving device. An implementation includes an infeed control system that controls the feeding of the stock material into the curving device by controlling the infeed system. The infeed control system may control various aspects of the stock of material being fed into the curving device including, but not limited to, the infeed speed, the infeed angle, the direction of feeding material (e.g., into or out of the curving device), the infeed force, the position of the stock of material, the position of various components of the infeed system, the offset of components of the infeed system and/or the stock of material, and the like. In some implementations, the infeed system includes one or more positioners, carriages, articulating arms, rollers, or the like, that feed each sheet of stock into the curving device, and each are collectively controllable by the infeed control system to ensure the desired infeed condition is met.

Turning back to FIGS. 5A and 5B, in some embodiments, the infeed system 504 includes a drive system, which may include a drive roll 510 with infeed rollers 512. The infeed rollers 512 can be individually driven by a drive system control system, which may be a component of the overall control system or independent from other control systems. In particular, the infeed rollers 512 can be differentially driven by the drive system control system (e.g., with some infeed rollers 512 being driven at a different rate than other infeed rollers 512) so as to cause the stock to rotate as it passes through the infeed rollers 512. Controlling the rotational speed of the infeed rollers 512 (in combination with other parameters described herein) can help implement rotational motion of the stock of material 501 about the peak of truncated cone 502 to be formed. The infeed rollers 512 may be used together with a curving device with steerable rollettes to steer the stock of material 501 in the desired rotating manner.

In the embodiment shown in FIGS. 5A—B, the infeed system 504 is able to translate along a direction parallel to the axis of the top roll 516 (i.e., bend axis), and to rotate in the plane. The infeed system 504 may be supported in the front (i.e., closer to the curving device 506) by a slewing ring (not shown; located behind stock of material 501 in FIG. 5A and underneath the material in FIG. 5B) that is able to rotate freely. The slewing ring may in turn be supported by a bearing (also not shown; located behind stock of material 501 in FIG. 5A) that runs on a shaft that may have an orientation that is parallel to the axis of the top roll 516. This may allow the infeed system 504 to both translate along a direction parallel to the axis of the top roll 516 and to rotate. The infeed system 504 may be supported in the rear (i.e., farther from the curving device 506) by an air bearing 530 (or other low friction motion device) that supports the infeed system 504 while allowing it to both rotate and translate with low friction.

In the embodiment shown in FIGS. 5A-5B, the position of the infeed system 504 can be controlled using at least two infeed actuators 514 that act as infeed adjustment mechanisms (although other numbers and forms of positioners may be used). Together, the infeed actuators 514 may be operable to set the position of the infeed system 504 along the x-axis and to set the angle of the infeed system 504, which may be done under the control of the infeed system control system. The infeed actuators 514 may include a hydraulic piston, pneumatic piston, servo, screw, actuator, rack and pinion, cable and pulley system, cam, electromagnetic drive, or other device capable of imparting the desired motion. Controlling the motion of the infeed system 504 via the infeed actuators 514 (in combination with other parameters described herein) can help implement rotational motion of the stock of material 501 about the peak 503 of the truncated cone 502 during the construction process.

To assist in the control of the motion of the stock of material 501, the individual rollettes 524 of the rollette banks 522 in the triple roll 516 can be controlled in various ways. In some implementations, the individual rollettes 524 can be steered by the control system. That is, the direction of motion imparted to the stock of material 501 by the rollettes 524 is controllable by setting the angles of the individual rollettes 524 with respect to the chassis of the triple roll 516. In particular, the rollers can modify the motion imparted to the stock of material by the infeed system 504.

In some implementations, the rollettes 524 are fixedly mounted, but the rotational speed of the rollers of the rollettes 524 is controllable. In some implementations, controlling the relative speeds of the rollers of the rollettes 524 can collectively impart rotational motion of the stock of material 501 about the peak 503 of the truncated cone 502.

Figure 11A:
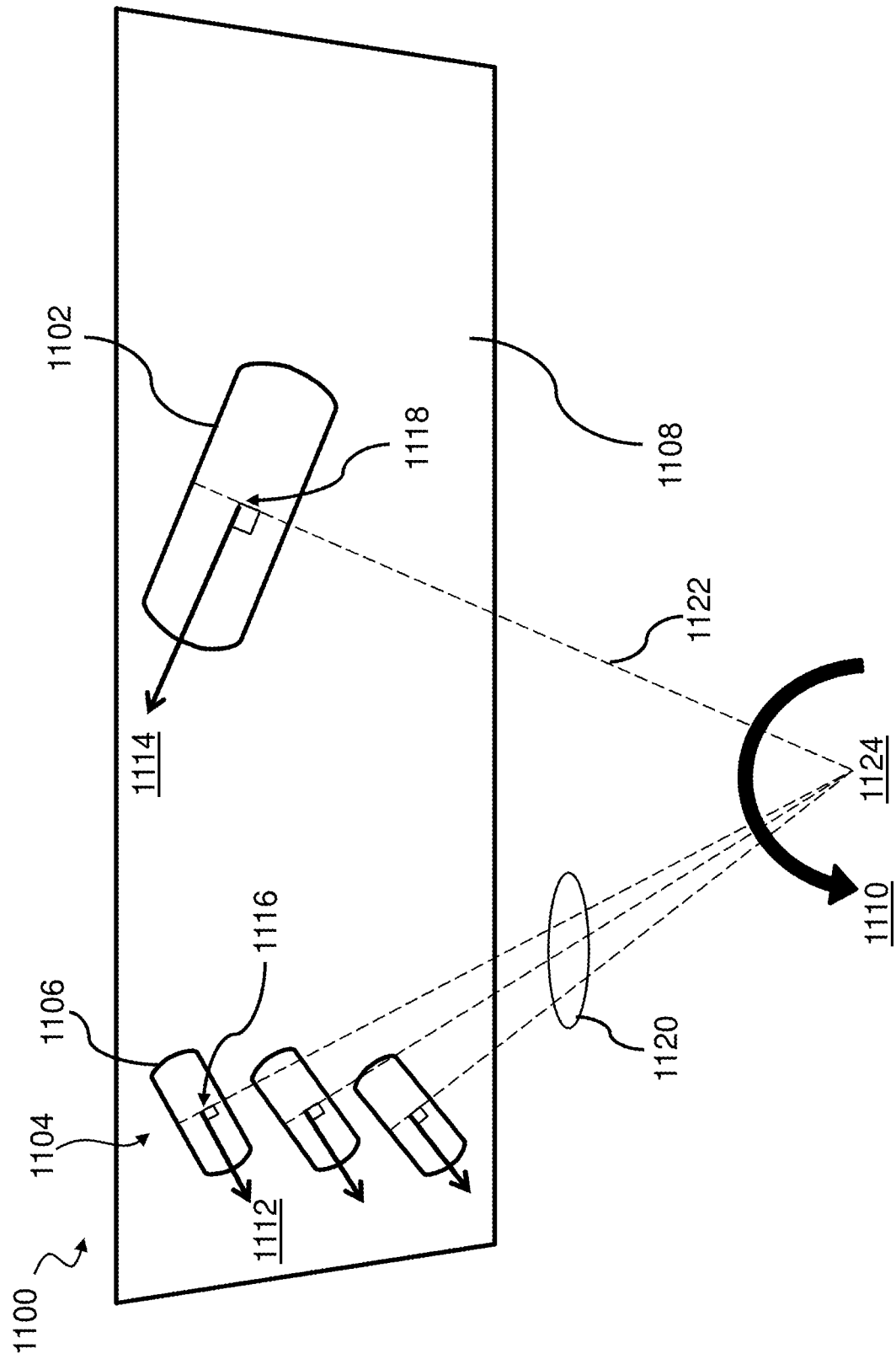

FIG. 11A depicts a system 1100 for sheet steering using a drive roll 1102 and a bank 1104 of steerable rollettes 1106. Specifically, FIG. 11A shows a schematic of a system 1100 by which a sheet of stock 1108 can be given rotational motion 1110 using a system with a positionable drive system (e.g., positionable drive roll 1102) and steerable rollettes 1106. The rolling directions for the rollettes 1106 are shown by the first arrows 1112 (where the rolling directions may be slightly different for each rollette 1106), and the rolling direction for the drive roll 1102 is shown by the second arrow 1114. Additionally, FIG. 11A shows contact areas 1116 on the rollettes 1106 (i.e., where the rollettes 1106 may contact the stock 1108, which may be a very small area, e.g., if the rollettes 1106 include rollers that are crowned), a contact area 1118 on the drive roll 1102 (i.e., where the drive roll 1102 may contact the stock 1108), lines 1120 perpendicular to the first arrows 1112 extending from the contact areas 1116 of the rollettes 1106, and lines 1122 perpendicular to the second arrow 1114 extending from the contact area 1118 of the drive roll 1102. In an implementation, if there is no (or negligible) slip, a sheet of stock 1108 will be driven along the rolling directions of all rolls in the system, including the drive roll 1102 and the individual rollettes 1106 (i.e., in the direction of the first and second arrows 1112, 1114). In general, it may only be necessary to have two non-parallel rolls to implement this system 1100. That is, when a single sheet of stock 1108 is acted on by two non-parallel rolls, the only way it can move along the rolling directions of both rolls without slipping is to rotate. In particular, the sheet of stock 1108 may rotate about the point 1124 located at the intersection of the lines 1120, 1122 that pass through the contact areas 1116, 1118 and are perpendicular to the direction of rolling 1112, 1114, as shown in FIG. 11A. If more than two rollers are present in the system (e.g., the bank 1104 shown with multiple rollettes 1106) the rollers should be positioned such that there is only one center of rotation, or else slipping may occur at one or more rollers and the stock 1108 movement will be poorly controlled. If two drive rolls 1102 are used as shown in FIG. 11B, the two drive rolls 1102 should also be positioned and their speeds controlled so that there is only one center of rotation at point 1124. In other words, if at least two drive rolls 1102 are used, the relative speeds of the drive rolls 1102 should be adjusted in order to maintain rotation about a single point 1124. Specifically, the speeds may be proportional to the distance of each drive roll 1102 from the axis of rotation. Also, the angles of the rollettes 1106 should be compatible with each other and with the drive rolls 1102, e.g., to maintain rotation about a single point 1124. In general, the components of the system (which may include all components referenced in this document) may be adjusted with the goal of having the stock of material rotate more or less about a single point. In other words, it may not be possible to perfectly align the stock of material and the components of the system (e.g., there may always be some slipping), so the components are adjusted in order to try to obtain optimal alignment where the stock of material rotates more or less about a single point.

The steering of the rollette banks may be accomplished, for example, with the cam plate steering described above with reference to FIGS. 3, 4A and 4B.

The implementations herein use various structures—positioners, single rollers, pairs or systems of rollers, etc.—to move the stock of material or contribute to moving the stock of material such that the net result is the stock of material moving rotationally with respect to the peak of the tapered structure as it moves through the curving device. These implementations illustrate only a few of the virtually infinite number of possibilities for accomplishing this result. In particular, the foregoing implementations do not exhaustively illustrate the full scope of the invention. Moreover, even for a specific configuration of equipment, in general there may be more than one way to control the various components so the net effect is to rotationally move the stock about the peak of the tapered structure on the stock's way to the curving device. Other control techniques are readily identifiable.

Implementations of a gap control system will now be described. "Gap control system" as used throughout this disclosure shall refer to any control system for correcting errors in the alignment of the edges of the stock of material when joining the edges of the stock of material, correcting gaps between the edges of the stock of material when joining the edges of the stock of material, and generally positioning the machinery and/or stock of material and/or tapered structure after the stock of material has been rolled through a portion of the curving device.

Even if the stock of material is fed correctly through the curving device (e.g., the bend roll in a triple roll), it may be beneficial to correct small errors in alignment and gap between corresponding edges of the stock of material after the edges are rolled and before they are joined together. This could be due to discrepancies in the geometry of the sheets of stock material, e.g., due to tolerances in the material forming processes, small errors in the infeed steering, small errors in the rolling process, etc. It may be beneficial to have additional systems that address gap and alignment errors after rolling and prior to joining edges of the stock of material together.

One of the purposes of the gap control system is to control the gap and alignment between a sheet of stock of material and the partially-completed tapered structure as they are joined together. For example, there may be at least three errors to address: in-plane gap error, out-of-plane gap error, and tangency alignment error. However, one skilled in the art will understand that the gap control system can be used to address more or less errors, or any combination of same.

Figure 12A:
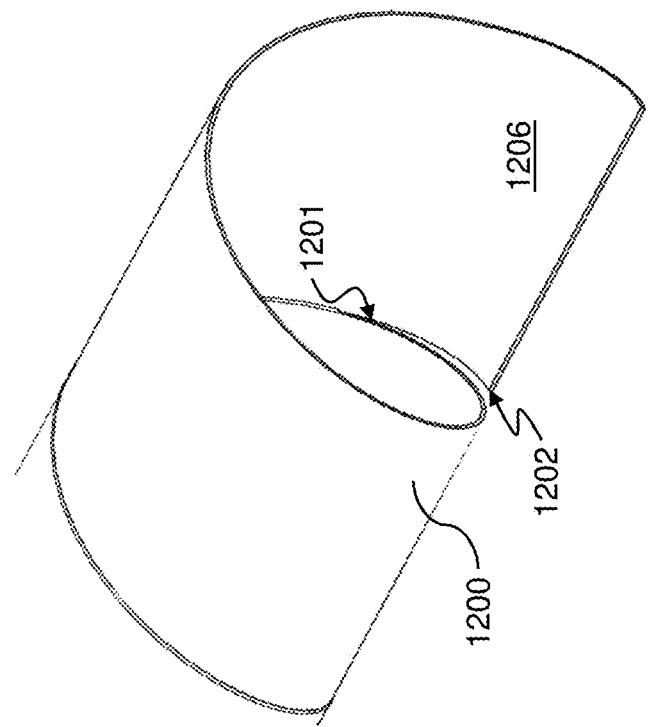
FIGS. 12A and 12B are schematic illustrations of an in-plane gap error.
Figure 12B:
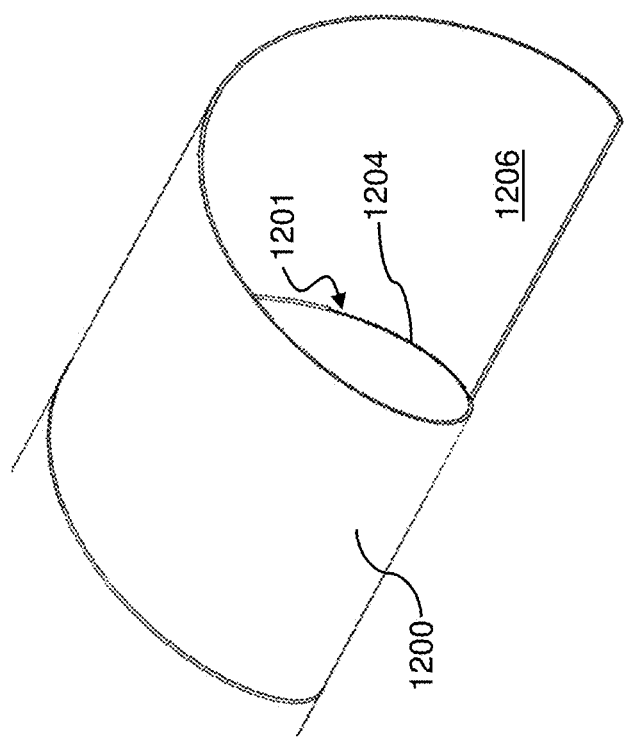

An example of in-plane gap error is illustrated in FIGS. 12A and 12B. FIG. 12A shows an example of a tapered structure 1200 (e.g., a truncated cone) with no error, while the tapered structure 1200 in FIG. 12B includes a gap error. The first arrow 1201 in FIGS. 12A and 12B points to the same location, where there is an error in FIG. 12B at this location. The error may be an in-plane weld gap error 1202. In FIG. 12A, the gap 1204 is even and the stock of material 1206 to be joined (e.g., welded) is aligned with the existing shape. In FIG. 12B, there is an in-plane gap error 1202, which means that, after joining is done at this location, the stock of material 1206 to be joined is disposed at an angle such that the gap is growing. An error also occurs if the gap is shrinking and is causing or will lead to an overlap and if the gap is "in the plane" of the existing curve—that is, the rolled material has the correct curvature to match the already-joined portion, but it's too far away (or too close).

An example of out-of-plane gap error is illustrated in FIGS. 13A and 13B. FIG. 13A shows an example with no error (FIGS. 13A and 13B depict a cylinder 1300, rather than a cone, so that it is easier to see the error when looking at the structure from an end). In FIG. 13A, the section shown viewed from an end looks like a complete circle because everything on the cylinder 1300 is aligned. FIG. 13B depicts a cylinder 1300 showing an example of an out-of-plane gap error 1302. The out-of-plane gap error 1302 occurs because, after joining is done at this location, the stock of material 1306 to be joined is curving away from the existing cylinder, opening up a gap 1304 that is out of the "plane" of the surface of the cylinder 1300 and causing ridges, bumps, dents (e.g., curving in to cause a dent or the like), or other surface errors on the surface of the tapered structure.

An example of tangency alignment error is illustrated in FIGS. 14A and 14B. FIG. 14A shows an example of a tapered structure 1400 (e.g., a truncated cone) with no error, while the tapered structure 1400 in FIG. 14B includes a tangency alignment error 1402. A tangency alignment error 1402 does not necessarily involve a gap, but rather it may involve an error in the alignment of the to-be-joined sheet surface 1404 with the existing sheet surface 1406 in a tapered structure 1400. As depicted in FIG. 14B, this type of error occurs when there is a surface misalignment. In other words, if the error was allowed to remain and the sheets were joined into place, the final structure (e.g., wind turbine tower) would appear bent, or it would have a dent, bulge, or the like.

The gap and alignment may be measured close to the joining location, with the intent being that the measurement may be located at a distance that is upstream of the joining such that adjustments can be made prior to joining. A method of measurement can include, but is not limited to, measuring with a laser line scanner (similar laser systems are used in gap-following automated welding systems), contact sensors (e.g., LVDTs or the like), a vision system using a video camera or similar, and so forth. It is also possible to measure the location of one of the edges relatively far away from the joining, for example, using a laser line scanner. In this case, only one edge may be measured, not a gap.

Implementations of a runout system will now be described. In general, gaps and misalignments may be corrected by translating and/or rotating the already-formed tapered structure relative to the rolled but not joined sheet that is held in the curving device (e.g., triple roll). To do this, one may either manipulate the rolled and joined tapered structure, or the rolled but unjoined sheet. One possible way to do this may be to hold the tapered structure in a runout system that supports the tapered structure after it has been joined, and to translate and rotate the curving device as it holds the rolled but unjoined sheet. Another way to do this is may be to hold the curving device fixed, and to manipulate the rolled and joined tapered structure using the runout system.

The runout system may have a number of mechanisms that are meant to prevent and/or correct the errors discussed herein. In an embodiment, a runout system has at least two subsystems—an "inboard" subsystem and an "outboard" subsystem. The inboard subsystem may be disposed close to the curving device and joining element. The outboard subsystem may be disposed close to the end of the tapered structure being formed, and support the end.

Figure 15:
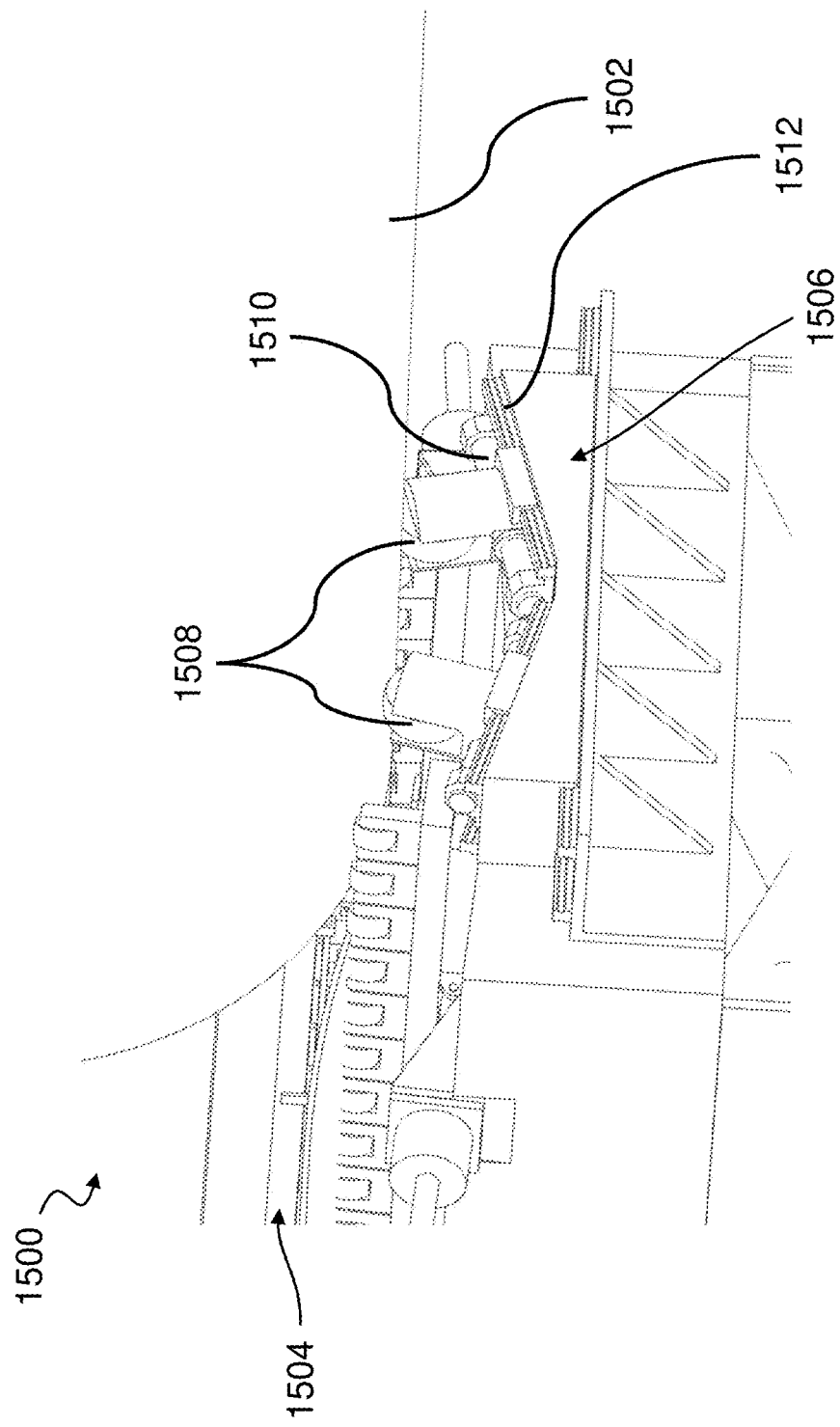
FIG. 15 is a close-up view of an inboard subsystem.
Figure 16:
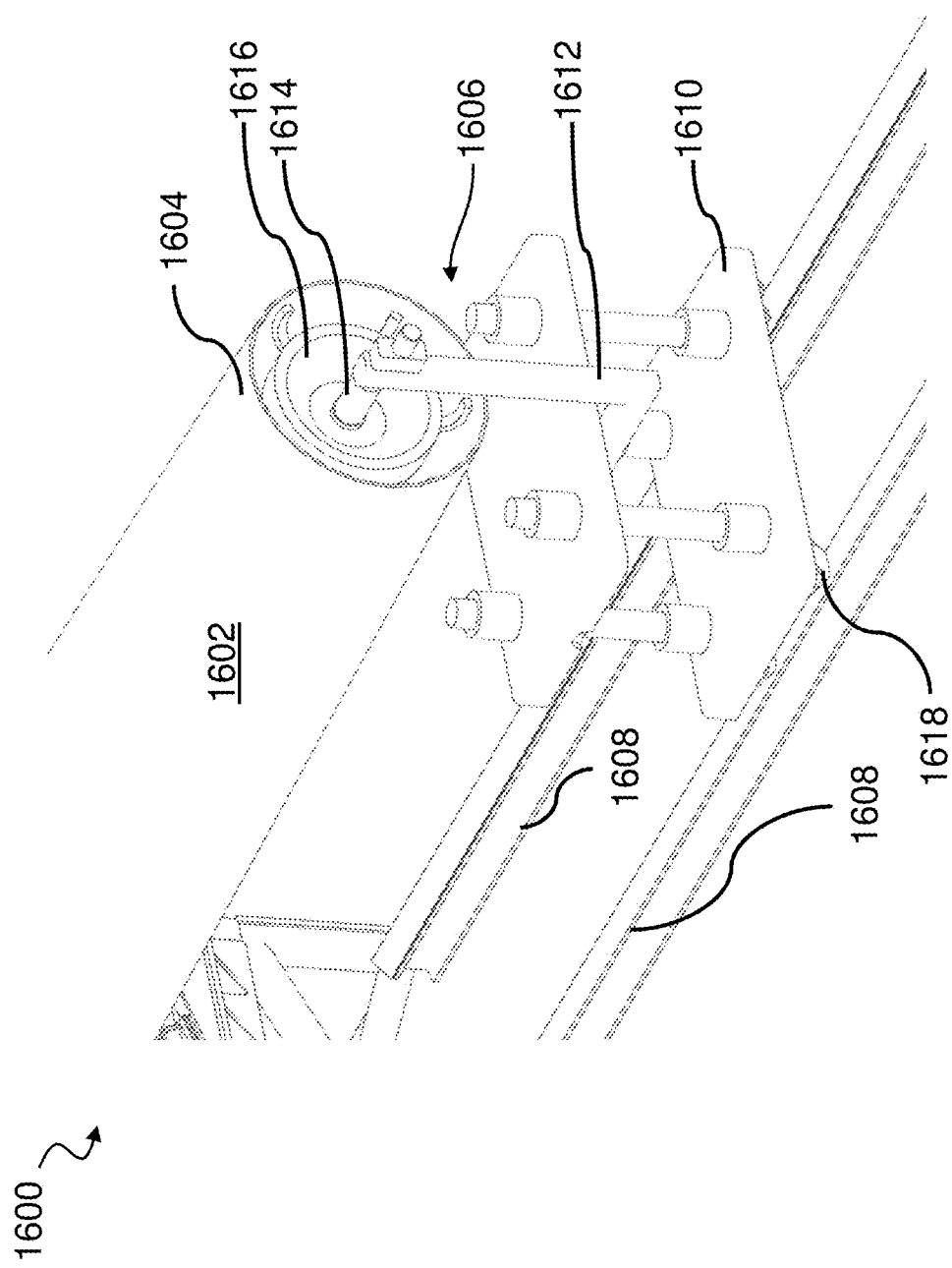
FIG. 16 is a close-up view of an outboard subsystem.

FIGS. 15 and 16 show an overview of an implementation of subsystems of a runout system, where FIG. 15 shows an inboard subsystem 1500 and FIG. 16 shows an outboard subsystem 1600.

As shown in FIG. 15, the inboard subsystem 1500 may support the tapered structure 1502 (e.g., truncated cone) as it is being formed, which may prevent the triple roll 1504 from having to support its weight. The inboard support mechanism 1506 may have an adjustable height, which can be used to address an out-of-plane gap error or a tangency error. For an out-of-plane gap error, the inboard 1500 and outboard 1600 systems (which can also move up and down in an embodiment) may move up and down together, keeping the slope of the tapered structure 1502, 1602 substantially the same but changing the out-of-plane gap. For a tangency error, the inboard 1500 and outboard 1600 systems may be moved vertically relative to each other, changing the angle of the tapered structure 1502, 1602.

The inboard support mechanism 1506 may include supports, such as support rollers 1508 or the like (e.g., pads, sliders, bearings, dampers, etc.). The support rollers 1508 may be positionable via a control (automatic or manual) or they may be passive. The supports may include dampers or the like, and they may be pivotable about a pivot point on a vertical support. The support rollers 1508 may allow the tapered structure 1502 to rotate easily relative to the support rollers 1508. The support rollers 1508 could be cylindrical, spherical (e.g., because the angle of the direction of the surface of the tapered structure 1502 relative to the support rollers 1508 changes as the tapered structure 1502 diameter changes, spherical rollers may account for this change), and the like. The supports may be disposed on a shaft 1510 or the like, where the shaft 1510 is movable from side to side (left and right). In addition, or in the alternative, the supports may be disposed on rails 1512, which allow the support rollers 1508 or the like to move from side to side. For example, the shaft 1510 may include a ball screw or the like, where the support rollers 1508 are slidable along the rails 1512 and are positioned by the ball screw. The position of the support rollers 1508 along the ball screw may determine the height of the support rollers 1508 and thus the height of the tapered structure 1502. This degree of freedom may also be used to passively adjust to changes in the position of the tapered structure 1502 being formed. In addition, or in the alternative, a degree of freedom that may be used to passively adjust to changes in position may be for the whole support structure 1506 moving from side to side on the rails 1512. The supports may move together, to adjust the position of the tapered structure 1502, or they may move relative to each other, to adjust to the changing diameter of the tapered structure 1502 and/or to apply a force on the tapered structure 1502. The supports may be passive, or they may include one or more actuators or the like to control the side to side movement of the supports. An actuator may be used to control the horizontal and/or vertical position of the tapered structure 1502 (e.g., in an implementation, if the supports are closer together, the tapered structure 1502 is higher) by moving the supports relative to each other. The actuator may also or instead be used to control the left/right position of the tapered structure 1502 by moving the supports together.

As shown in FIG. 16, the outboard subsystem 1600 may support the end 1604 of the tapered structure 1602, and may include mechanisms for addressing the gap and alignment errors. Some of these mechanisms are described below.

The outboard support 1606 of the outboard subsystem 1600 may move up and down. This (in tandem with height adjustment of the inboard system 1500) can address an out-of-plane gap error. This movement can also be used to address a tangency error—for example, when the height of the inboard system 1500 is kept fixed, adjusting the height of the outboard support 1606 may change the angle of the tapered structure 1502, 1602, so it can be brought into alignment.

The outboard support 1606 of the outboard subsystem 1600 may move side to side (perpendicular to the tracks 1608 shown in FIG. 16, i.e., left and right). This movement can be used to correct an in-plane gap error.

The outboard support 1606 of the outboard subsystem 1600 may be used to torque or twist the tapered structure

1602 around its axis. This twisting is another method for correcting an out-of-plane error, i.e., the twisting can be used to "wind-up" or "unwind" the to-be-joined sheet, thereby changing its diameter and bringing it into alignment. The outboard subsystem 1600 may also have active control of its travel away from the curving device as the tapered structure 1602 is being formed. For example, yet another possible degree of freedom is control of the travel of the outboard cart 1610 along the tracks 1608. This control could potentially address in-plane gaps by moving the tapered structure 1602 toward and away from the curving device which can open and close gaps. This movement can also provide a force on the tapered structure 1602, which may be a pushing force toward the curving device or a pulling force away from the curving device. The cart 1610 may also include a brake, which may be an actively controlled brake. Also, an embodiment may include a passive runout system. A skilled artisan will understand that the components of the outboard subsystem 1600 may be used to correct errors other than the errors specifically mentioned herein. For example, raising and lowering the outboard support 1606 can correct in-plane errors as well as out-of-plane errors. In addition, components of the other systems described herein may be used to correct errors other than the errors specifically mentioned herein.

In an embodiment, the outboard support 1606 is disposed toward the end 1604 of the tapered structure 1602 as shown in FIG. 16. However, in other embodiments, the outboard support may be disposed at other locations (not shown), including, but not limited to, toward the center of the tapered structure or towards an end of the tapered structure that is closest to the curving device.

The outboard support 1606 may include a vertical support post 1612 and a horizontal support arm 1614, where the support post 1612 is engaged with the cart 1610. At an end of the horizontal support arm 1614 there may be a cone engagement mechanism 1616, which includes a support structure for both supporting the tapered structure 1602 and/or grabbing the tapered structure 1602.

In an implementation, the cone engagement mechanism 1616 locks onto the tapered structure 1602 such that it can move and/or twist the tapered structure 1200 without becoming disengaged. This may be accomplished through a spindle or spindle-like structure, and/or using clamps, bolts, cables, clips, couplings, docks, dowels, a friction fit, gibs, hooks, joints, latches, locks, lugs, pins, screws, sliders, snaps, and the like. For example, a grabber that supports the tapered structure 1602 from the inside and allows it to rotate may be provided. The grabber may be controlled to lock the tapered structure 1602, release the tapered structure 1602, rotate the tapered structure 1602, and the like.

The outboard subsystem 1600 may include a cart 1610 that allows the outboard subsystem 1600 to be mobile. The cart 1610 may include wheels 1618 or the like that can ride along the tracks 1608 or the like. An implementation may only include wheels 1618 or the like, without any tracks (not shown). The cart 1610 may also or instead include slides, which may slide along a track or slide freely (i.e., on the floor). The slides may include a mechanism for decreasing sliding friction such as low friction materials (e.g. Teflon), grease, rolling element bearings, air bearings, and the like.

Further implementations of a control system will now be discussed.

The construction systems described herein for forming a tapered structure may include a control system that is able to control one or more components of the construction system. For example, a control system may include a sensor, or multiple sensors, that provide feedback on a component or multiple components of the construction system and/or on the tapered structure being formed. The construction system may include one or more adjustment mechanisms that can automatically position a component or multiple components of the construction system and/or the tapered structure being formed. Unless explicitly stated, or otherwise clear from the text, as used throughout this document, the adjustment of the stock of material, or the adjustment of the tapered structure, shall include any adjustment to the material at any stage during the construction of the tapered structure (before, during, or after the formation of the tapered structure). The automatic positioning may be based off of the feedback obtained from the sensors, and/or it may be based off of a model used to form the desired tapered structure. For example, in an implementation that includes a triple roll, the adjustment mechanism may automatically position at least one of the rolls of the triple roll to adjust the shape of a tapered structure being formed. The automatic positioning may allow for a substantially continuous change in the diameter of the structure being formed such that it is tapered. The adjustment mechanism may include any means known by skilled artisans, including without limitation hydraulic pistons, pneumatic pistons, servos, screws, actuators, rack and pinion systems, cable and pulley systems, cams, electromagnetic drives, robotic arms, rollers, drivers, or the like, or combinations of any of the foregoing or other device capable of imparting the desired motion.

The feedback from the sensors may be provided to a computer and/or controller, which may then send signals to an adjustment mechanism (or multiple adjustment mechanisms) for automatically positioning the components of the construction system, e.g., one of the rolls of the triple roll. The feedback may include many different types of feedback including, but not limited to, one or more of: a position of a component of the construction system (e.g., one of the rolls of the triple roll, and/or a distance between at least two rolls of the triple roll, an angle of a component of the construction system relative to another component and/or the tapered structure being formed, and so on), geometric data of the tapered structure being formed (e.g., a diameter, a radius of curvature, a taper angle, an in-plane weld gap, an out-of-plane weld gap, an edge position, a distance of the "center" of any a section of the tapered structure from an axis of the tapered structure, and so on), force data (e.g., a force needed to complete an action of the machine for forming a tapered structure, where the actions include, but are not limited to, closing weld gaps, straightening the tapered structure for tangency, adjusting an angle of at least one of the plurality of rolls, moving at least one of the plurality of rolls, and driving a stock of material into or through the machine for forming a tapered structure), and the like.

The control system may further include a model for forming a tapered structure. The model may be a mathematical and/or computer model. The model as described herein may include an empirical model (e.g., a purely empirical model), a look-up table based on a model, a fundamental concepts model, or any combination of these models. The model outputs may be based on theoretical or mathematical analysis, empirical measurements, fitting factors, other factors, and/or other parameters that may affect the machine operation. The model may compute results during machine operation. The model may include previously computed results that are stored and then accessed during machine operation. The model may include positions for one or more of the components of the construction system (e.g., the positions of the rolls included in the triple roll). The model may also or instead include geometric information for the tapered structure being formed. The geometric information may include positions of coordinates and/or features of the tapered structure relative to one or more components of the construction system and/or relative to each other. The model may include a model for ideal edge positions of a stock of material, where the model includes positions of the curving device and the tapered structure based on the feedback provided by an edge position sensor. The adjustment mechanism may be configured to automatically position one or more components of the construction system (e.g., at least one roll of the triple roll) based on output from the model. The adjustment mechanism may also be configured to automatically position one or more components of the construction system based on a combination of the feedback from the sensors and the model.

The adjustment mechanism or mechanisms may be configured to position one or more components of the construction system (e.g., at least one roll of the triple roll) along a sloped path. The adjustment mechanism or mechanisms may be configured to position one or more components of the construction system (e.g., at least one roll of the triple roll) along a curved path. The adjustment mechanism or mechanisms may be configured to position an angle of one or more components of the construction system (e.g., at least one roll of the triple roll). The adjustment mechanism or mechanisms may be configured to position the tapered structure in any manner as described herein or which would be reasonably apparent to those of ordinary skill.

The construction system may include a triple roll, where the triple roll includes three rollette banks, and the rollette banks include a plurality of individual rollettes, which may include rollers in an implementation. The adjustment mechanism may be configured to adjust an angle of a rollette bank. The adjustment mechanism may be configured to adjust an angle of the plurality of rollettes. Each individual rollette may be capable of being steered, and adjustment mechanism or mechanisms may be configured to do the steering.

The adjustment mechanism may be configured to position the rolls of the triple roll independently. For example, multiple adjustment mechanisms may be present, where each is configured to position a corresponding roll of the triple roll.

An implementation may include a stock of material for forming into the tapered structure, where the stock of material is fed into the machine for forming a tapered structure and is formed into the tapered structure by the triple roll. The adjustment mechanism may be configured to automatically adjust the angles of at least one set of rollettes to maintain the stock of material in a proper position for forming into a tapered structure. The adjustment mechanism may be configured to automatically adjust the angle of at least one set of rollettes to compensate for slipping of the stock of material.

In an implementation, the infeed system receives the stock material from a stock material source, a roll of stock sheets, a magazine of stock, or the like, to the curving device. Thus, together, the infeed system and the curving device may take a stock of material and curve the material into a desired shape, which may be a substantially conical shape with a radius that changes throughout its length. In an implementation, the curving device includes a triple roll, where the triple roll includes at least three rollette banks that include a plurality of rollettes. The three rollette banks of the triple roll may include at least two bottom rollette banks, where one acts as an inlet rollette bank and the other acts as an outlet rollette bank. In an implementation, the inlet and outlet rollette banks are able to move in order to control the shape of the material being formed. Controlling the shape of the material being formed may be accomplished through controlling the diameter of the material being formed.

A control system of an implementation includes feedback, which may be based upon any one of a number of criteria, or any combination of criteria. For example, the feedback may be based upon geometric data. The geometric data may be obtained from the shape being formed, which may be a tapered structure (e.g., a cone). The geometric data may include, but is not limited to, a measurement of the diameter, radius of curvature, taper angle, weld gap (which may be a gap that is in the plane of the material being joined, or out of the plane, or both), and a distance of a section of the tapered structure from an axis of the tapered structure (which may be measured from the "center" of any section to the axis). Any one of these measurements may be used, or any other combination of these measurements may be used, as feedback for the control system.

The feedback may also include geometric data from one or more of the components of the curving device, including, but not limited to, the rolls, the rollers, the rollette banks, the rollettes, the positioners, the wheels, the drive system, and so on. The feedback may also include geometric data from one or more of the components of the infeed system or runout system as described herein, or can be envisioned from this disclosure. This geometric data may also include relative data from one component to another, for example, a distance between components, an angle between components, and the like.

In an implementation, the feedback may also or instead include force data. The force data may be obtained from the shape being formed, which may be a tapered structure (e.g., a cone). The force data may also or instead include force data obtained from the components of the construction system. Examples of the force data include, but are not limited to, forces that may be required to complete an action of the construction system for forming a tapered structure, such as the forces needed to close weld gaps, straighten the tapered structure for tangency, adjust the angle of a roll or rolls, move a roll or rolls, drive a material into or through the construction system, and the like. Any one or all of these forces may be used, or any other combination of these forces may be used as feedback for the control system.

In an implementation, the feedback data is obtained by sensors. A variety of sensors may be usefully incorporated into the control systems described herein as will be readily apparent to one skilled in the art. For example, the sensors may include, but are not limited to, position sensors (e.g., an edge position sensor), angle sensors, displacement sensors, distance sensors, speed sensors, acceleration sensors, optical sensors, light sensors, imaging sensors, pressure sensors, force sensors, torque sensors, level sensors, weight sensors, proximity sensors, presence (or absence) sensors, magnetic sensors, radio sensors, acoustic sensors, vibration sensors, and the like. The sensors may include a singular sensor or numerous sensors.

The sensors may also include an imaging device and image processing circuitry to capture an image of the tapered structure being formed or components of the construction system and analyze the image to evaluate the shape, position, etc. of the tapered structure being formed or components of the construction system. The sensors may also or instead include at least one video camera. The video camera may generally capture images of the construction system and/or the tapered structure being formed. The video camera may provide a remote video feed through a network interface, which feed may be available to operators through a user interface maintained by, e.g., remote hardware such as a server or within a web page provided by a web server.

The construction system may include a sensor that detects a position of the stock of material along the path of construction (from the infeed system, to the curving device, to the runout system) or the position at any area of the system.

The sensors may also include more complex sensing and processing systems or subsystems, such as a three-dimensional scanner using optical techniques (e.g., stereoscopic imaging, or shape from motion imaging), structured light techniques, or any other suitable sensing and processing hardware that might extract three-dimensional information from the constructions system and/or tapered structure. In another aspect, the sensors may include a machine vision system that captures images and analyzes image content to obtain information, e.g., the status of a tapered structure being formed. The machine vision system may support a variety of imaging-based automatic inspection, process control, and/or robotic guidance functions for the construction system including without limitation pass/fail decisions, error detection (and corresponding audible or visual alerts), shape detection, position detection, orientation detection, collision avoidance, and so forth.

In an embodiment, a sensor provides feedback that includes the radius of the tapered structure being formed. The construction system may then be controlled by the control system to maintain a substantially continuous radius adjustment in the tapered structure in order to form a substantially cone shaped object. In other words, the radius adjustment may be automatically controlled in order to create a constantly changing diameter, as would be done for a tapered shape.

An implementation includes adjustable triple roll banks for rolling tapered cones. An implementation includes substantially continuously adjusting the machinery, which may include adjusting the triple roll bank, during the rolling process in order to substantially continuously adjust the diameter of a tapered structure being formed. The diameter of the tapered structure being formed may be varied by moving the rolls, where moving the rolls may be a reaction to the changing diameter.

An embodiment may include controlling the angles of the rollettes themselves. A triple roll for forming a tapered structure may include rollette banks that are comprised of multiple individual rollers or rollettes. These rollette banks may replace the rollers in a conventional roll bending process. The heading angles of individual rollettes can be steered in an implementation, and the rollettes in an implementation are actively and continuously steered thus providing continuous control over stock motion. In an implementation, the rollettes also serve to steer the material as it passes through the triple roll.

The rollette angle may be controlled for the following reasons. The triple roll (interfacing with the stock of material/sheet through the rollettes) is one of the means for controlling the bulk motion of the incoming feed stock and formed tapered structure. By steering the rollettes (alone, or in conjunction with other modules) in an appropriate manner, the incoming feed stock carries out a specific motion for rolling tapered structures.

In an embodiment, rollettes can be steered to control weld gap. In an embodiment, rollettes can be steered to shift the stock towards or away from the throat of the triple roll to maintain proper sheet position within the triple roll. Rollettes may also be steered to compensate for side slip.

The rollettes may be steered individually with electric motors, gears, racks, cams, linkages, screws, chains, belts, hydraulics, pneumatics, magnetically, manually, friction drives, traction drives, thermally, and the like.

All or some of the rollettes on a bank of rollettes may be steered together but through angles individual to each rollette. Specifically, in an implementation, for rollettes driven together, each individual rollette angle corresponds to a particular, but not the same, angle for all the other rollettes. These rollette groups may be steered with motors, gears, racks, cams, linkages, screws, chains, belts, hydraulics, pneumatics, magnetically, manually, friction drives, traction drives, thermally, and the like.

All or some of the rollettes on a particular rollette bank may be steered all together through the same angles. These rollette groups may be steered with motors, gears, racks, cams, linkages, screws, chains, belts, hydraulics, pneumatics, magnetically, manually, friction drives, traction drives, thermally, and the like.

In an implementation, the rollettes on a particular rollette bank may be steered using a cam plate as described above. The cam plate may have different profiles for each cam, resulting in different motions for each rollette, or the same profiles for one or more cams, resulting in the same steering motion for the corresponding rollettes. The profiles in the cam plate may correspond to the desired rollette motions (based on a model) for rolling a particular cone. Or, the profiles may correspond to another relationship between the cam plate position and rollette angles that allows the control system to adjust the rollette angles, i.e., there could be a linear relationship (moving the cam a certain distance causes the rollette heading angle to change proportionally), etc.

In an implementation, one or all of an infeed positioning system, curving device positioning system, and a runout positioning system may be used to control the distance and angle between two corresponding edges of the stock as the edges are joined. In an implementation, the formed and joined tapered structure is held fixed in the runout system, and the curving device, along with the section of stock that is held in the curving device, is positioned relative to the formed and joined structure. The curving device may be translated relative to the formed and joined structure, in order to close in-plane gaps between edges of the stock so that they can be joined. The curving device may also rotate relative to the formed and joined structure, e.g., in order to close out-of-plane gaps and correct tangency mismatches between edges.

Figure 17:
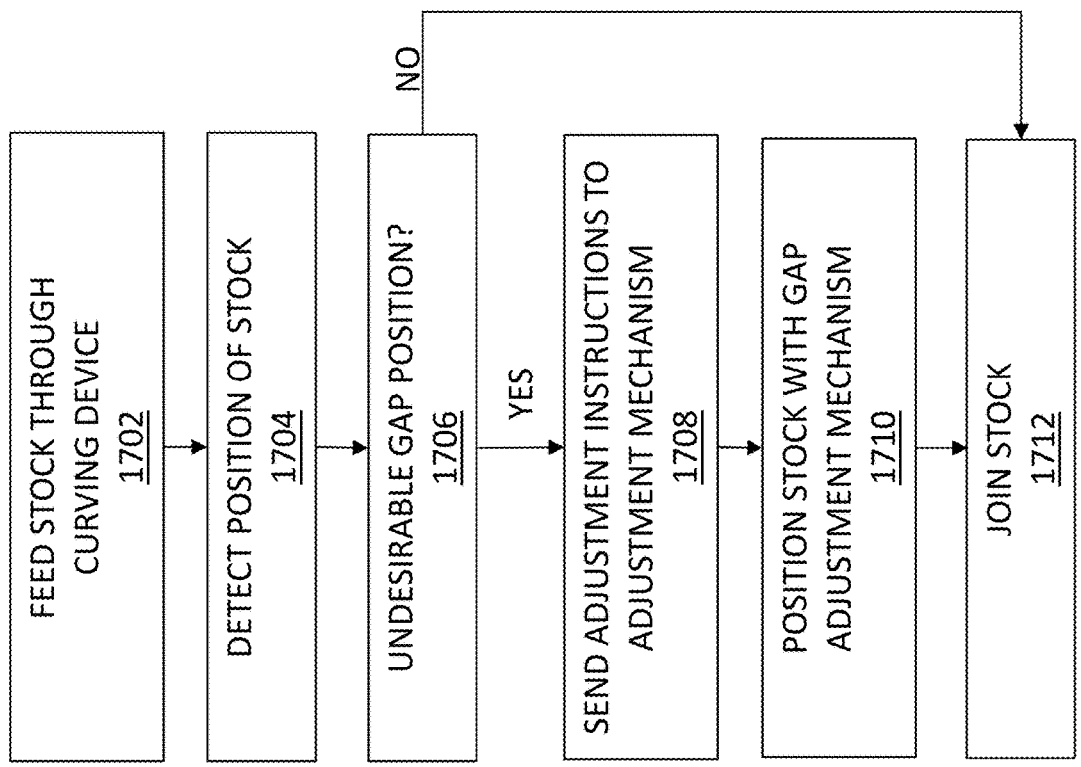
FIG. 17 is a flow chart of a method for weld gap adjustment.

FIG. 17 shows a flow chart 1700 for a method for weld gap adjustment according to an implementation.

As shown in step 1702, the method may include feeding a stock of material into and through a curving device. The feeding of the stock of material may be accomplished through any of the means described herein, including, without limitation an infeed system that may include a drive roll and an infeed adjustment mechanism. The curving device may include a triple roll.

As shown in step 1704, the method may include detecting the position of the stock of material. This may include detecting at least one edge of the stock of material. The detection may be made by a sensor. Additionally or alternatively, this step may include detecting the position of a component of the infeed system or curving device.

As shown in step 1706, the method may include determining whether the position indicates an undesirable gap condition. This step may include sending the position to a gap error controller, where the controller determines whether the position indicates an undesirable gap condition.

The determination may also be accomplished by comparing the sensed/detected position to a known ideal position, where the known ideal position may be part of a model, a known measurement, a predetermined value, a position from previous operations of the system or method. The undesirable gap position may be any of the errors described herein, e.g., an inconsistency in a weld gap, an angular alignment error, a planar alignment error, etc.

If an undesirable gap position is detected, the method may proceed to step 1708, and if an undesirable gap position is not detected, the method may skip to step 1712.

As shown in step 1708, the method may include sending adjustment instructions to a gap adjustment mechanism. The adjustment instructions may be sent by a controller, e.g., the gap error controller. The adjustment instructions may include a position of a component of the system (e.g., the infeed system or the curving device), a position of the stock of material, a position or movement of an adjustment mechanism, and the like. The gap adjustment mechanism may be any adjustment mechanism described herein (or combination thereof) that can adjust a component of the systems described herein including, without limitation, an infeed adjustment mechanism, a drive roll adjustment mechanism, a rollette steering mechanism, a runout adjustment mechanism, and so on. In other words, the adjustment instructions may compensate for the positioning error. For example, the positioning error may include an inconsistency in a weld gap included in the stock of material, and the adjustment instructions may include instructions to position the stock of material such that a consistent weld gap is formed during the welding of the stock of material. The positioning error may include a planar alignment error in the stock of material, and the adjustment instructions may include instructions to position the stock of material such that an edge of the stock of material is substantially adjacent to an opposing edge of the stock of material as they are joined. The positioning error may include an angular alignment error detected in the stock of material, and the adjustment instructions may include instructions to position the stock of material such that an edge of the stock of material is substantially parallel with an opposing edge of the stock of material as they are joined.

As shown in step 1710, the method may include positioning the stock of material with the gap adjustment mechanism. This step may include any of the positioning components, systems, and methods described herein.

As shown in step 1712, the method may include joining the stock of material using the joining elements. This may include joining corresponding edges of the stock of material together, for example, using a welder. The joining may include substantially continuously joining the stock of material as it is rolled through the curving device, or after it is rolled through the curving device and into a runout system to form a tapered structure in the runout system.

Figure 18:
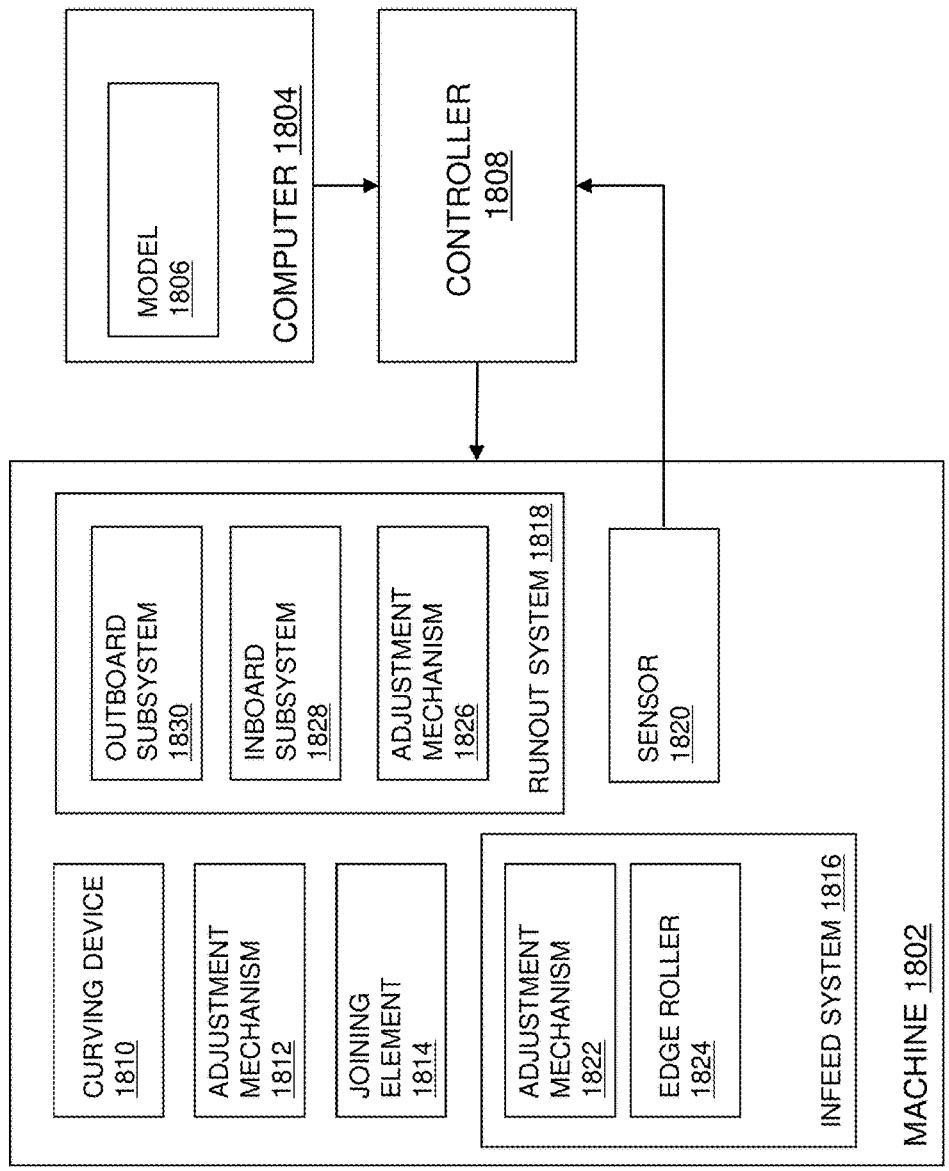
FIG. 18 is a block diagram for a control system.

FIG. 18 shows a block diagram for a control system 1800 according to an implementation. Specifically, FIG. 18 shows a machine 1802, which may be a machine for forming a tapered structure, a computer 1804, which may include a model 1806, and a controller 1808.

The machine 1802 may include a curving device 1810, an adjustment mechanism 1812, a joining element 1814, an infeed system 1816, a runout system 1818, and at least one sensor 1820.

The curving device 1810 may be any described herein, e.g., a triple roll. The triple roll may have at least three rolls including at least one bend roll and at least two guide rolls. The guide rolls may include rollette banks having a plurality of rollettes.

The adjustment mechanism 1812 may be any means for adjustment described herein, and it may be suitable for adjusting any component of the machine 1802, e.g., a component of the curving device 1810 (e.g., one or more of the rolls of the triple roll). In an implementation including a triple roll, the adjustment mechanism 1812 may be configured to position at least one of the rolls, where a diameter of a tapered structure being formed is controlled by relative positions of the rolls. The adjustment mechanism 1812 may be configured to translate at least one of the rolls in a triple roll relative to another one of the rolls without changing an angle of the roll in order to substantially continuously adjust the diameter of the tapered structure being formed. The adjustment mechanism 1812 may also or instead be configured to position an angle of at least one of the rolls with respect to another one of the rolls in a triple roll. The adjustment mechanism 1812 may include numerous adjustment mechanisms, e.g., one adjustment mechanism configured to position a corresponding roll in a triple roll. The adjustment mechanism 1822 may be configured to position the stock of material such that the stock of material rotates about a peak of the tapered structure or an end of the tapered structure.

The joining element 1814 may be any described herein, e.g., a welder. The joining element 1814 may be controllable and movable.

The infeed system 1816 may include its own adjustment mechanism 1822 (e.g., an infeed adjustment mechanism configured to position a stock of material as it is fed into the curving device), or it may use the adjustment mechanism 1812 described above. The infeed system 1816 may include any of the components described herein, e.g., a drive roll. The infeed system 1816 may also include at least one edge roller 1824 configured to constrain positions of edges of a stock of material fed into or through the curving device 1810, where the adjustment mechanism 1822 is configured to position the edge roller 1824.

The runout system 1818 may include its own adjustment mechanism 1826, or it may use the adjustment mechanism 1812 described above. The runout system 1818 may include any of the components described herein, e.g., any of the components associated with the inboard subsystem 1828 and the outboard subsystem 1830.

The sensor 1820 may be any sensor described herein, and the sensor 1820 may be part of the machine 1802 or a separate component. The sensor 1820 may provide feedback to the controller 1808, which may use the feedback to send control signals to components of the machine 1802. The feedback may include geometric data of the tapered structure being formed, where the geometric data includes, without limitation, a diameter, a radius of curvature, a taper angle, a weld gap, a distance of a section of the tapered structure from an axis of the tapered structure, and the like. The feedback may also or instead include force data, including, without limitation, a force needed to complete an action, where the action includes at least one of: closing weld gaps, straightening the tapered structure for tangency, adjusting an angle of one of the rolls in a triple roll, moving a roll, and driving the stock of material into or through the machine for forming a tapered structure.

The model 1806 may be any model described herein, and the model 1806 may be disposed on or implemented by the computer 1804. Alternatively, the model 1806 may be stored on or implemented by the controller 1808, or a processor associated with the controller 1808. The model 1806 may send information to the controller 1808, which may use the information to send control signals to components of the machine 1802. The model 1806 may generally include a model for forming a tapered structure that includes, without limitation, relative positions of the rolls of a triple roll for desired tapered structure diameters, relative positions of the stock of material as it is fed into or through the machine for forming a tapered structure, and the like.

The controller 1808 may send control signals to one or more components of the machine 1802 based on the feedback from the sensor 1820 alone, the information from the model 1806 alone, information from more than one sensor or model, or any combination thereof. The controller 1808 may be configured to receive the feedback from the sensor 1820. The controller 1808 may also be configured to send a control signal based on the feedback to any of the components of the system 1800, e.g., the adjustment mechanisms 1812, 1822, 1826 for positioning a component of the machine 1802 or a stock of material being formed into a tapered structure.

The controller 1808 may be electrically or otherwise coupled in a communicating relationship with one or more components of the system 1800. The controller 1808 may include any combination of software and/or processing circuitry suitable for controlling the various components of the system 1800 described herein including without limitation microprocessors, microcontrollers, application-specific integrated circuits, programmable gate arrays, and any other digital and/or analog components, as well as combinations of the foregoing, along with inputs and outputs for transceiving control signals, power signals, sensor signals, and so forth. In one aspect, this may include circuitry directly and physically associated with the components of the system 1800, such as a processor. In another aspect, this may be a processor, which may be associated with a personal computer or other computing device coupled to the components of the system 1800, e.g., through a wired or wireless connection. Similarly, various functions described herein may be allocated between a controller, processor, and a separate computer. All such computing devices and environments are intended to fall within the meaning of the term "controller" or "processor" as used herein, unless a different meaning is explicitly provided or otherwise clear from the context.

FIG. 19 shows a method 1900 for controlling the formation of a tapered structure.

As shown in step 1902, the method 1900 may include sensing an attribute with a sensor on a system for forming a tapered structure. The attribute may be a geometric attribute of the tapered structure being formed, a geometric attribute of the system for forming a tapered structure, a force attribute of the tapered structure being formed, a force attribute of the system for forming a tapered structure, and the like, or any combination thereof. The sensor may include any sensor described herein or otherwise known by a skilled artisan.

The system for forming a tapered structure may include a curving device, which may be a triple roll having at least three rolls including at least one bend roll and at least two guide rolls, where the guide rolls include rollette banks having a plurality of rollettes. The system for forming a tapered structure may further include an adjustment mechanism configured to position at least one of the rolls, where a diameter of the tapered structure being formed is controlled by relative positions of the rolls. The system for forming a tapered structure may further include a joining element for joining edges of a stock of material together as the stock of material is rolled through the curving device (e.g., the triple roll) to form the tapered structure.

As shown in step 1904, the method 1900 may include sending feedback from the sensor to a controller. The feedback may be based on the sensed attributes discussed above. The controller may be any discussed herein or otherwise known by a skilled artisan. The controller may be remote to the system or integral with the system. The feedback may be sent to the controller via a sensor signal, and the feedback may be processed/analyzed at the controller or at another location/device.

As shown in step 1906, the method 1900 may include sending adjustment instructions to the adjustment mechanism. The adjustment instructions may be sent from the controller, or from another component of the system. The adjustment instructions may be based on the feedback. The adjustment mechanism may be any of the adjustment mechanisms discussed herein, i.e., capable of adjusting a position of the stock of material (including the tapered structure before, during, and after formation), and/or a component of the system/machine for forming a tapered structure.

As shown in step 1908, the method 1900 may include adjusting a position of a roll. This may include adjusting a position of at least one of the rolls of the triple roll, or any component of the curving device, with the adjustment mechanism based on the adjustment instructions.

FIG. 20 shows a method 2000 for controlling the formation of a tapered structure.

As shown in step 2002, the method 2000 may include sensing a position of a stock of material with a sensor on a system for forming a tapered structure. The stock of material may be the stock for forming into a tapered structure or the tapered structure itself (including the tapered structure before, during, and after formation).

The system for forming a tapered structure may be similar to that described herein, for example with reference to FIG. 19, and may also or instead include an infeed adjustment mechanism configured to position the stock of material as it is fed into at least one of the rolls, the stock of material forming the tapered structure as it is rolled through the curving device. The infeed adjustment mechanism may include any means for adjusting any component of the infeed system, including the stock of material, or moving another component of the system thereby positioning the stock of material as it is fed into the curving device.

As shown in step 2004, the method 2000 may include sending feedback from the sensor to a controller. The feedback may be based on the position of the stock of material.

As shown in step 2006, the method 2000 may include sending adjustment instructions to the infeed adjustment mechanism. The adjustment instructions may be sent from the controller, or from another component of the system. The adjustment instructions may be based on the feedback.

As shown in step 2008, the method 2000 may include adjusting a position of the stock of material. This may include adjusting a position of the stock of material as it is fed into or through the system for forming a tapered structure based on the adjustment instructions.

FIG. 21 shows a method 2100 for controlling the formation of a tapered structure.

As shown in step 2102, the method 2100 may include sensing a position of an edge of a stock of material with an edge position sensor. The stock of material may be the stock for forming into a tapered structure or the tapered structure itself (including the tapered structure before, during, and after formation). The system for forming a tapered structure may include a rolling assembly, a joining element, a runout system, and an adjustment mechanism.

As shown in step 2104, the method 2100 may include sending feedback from the edge position sensor to a controller. The feedback may be based on the position of the edge of the stock of material.

As shown in step 2106, the method 2100 may include sending adjustment instructions to the adjustment mechanism. The adjustment instructions may be sent from the controller, or from another component of the system. The adjustment instructions may be based on the feedback.

As shown in step 2108, the method 2100 may include adjusting a position of the tapered structure (e.g., before, during, or after formation). This may include adjusting a position of the tapered structure relative to the rolling assembly using the adjustment mechanism based on the adjustment instructions, e.g., after the stock of material has been through the rolling assembly.

Figure 22:
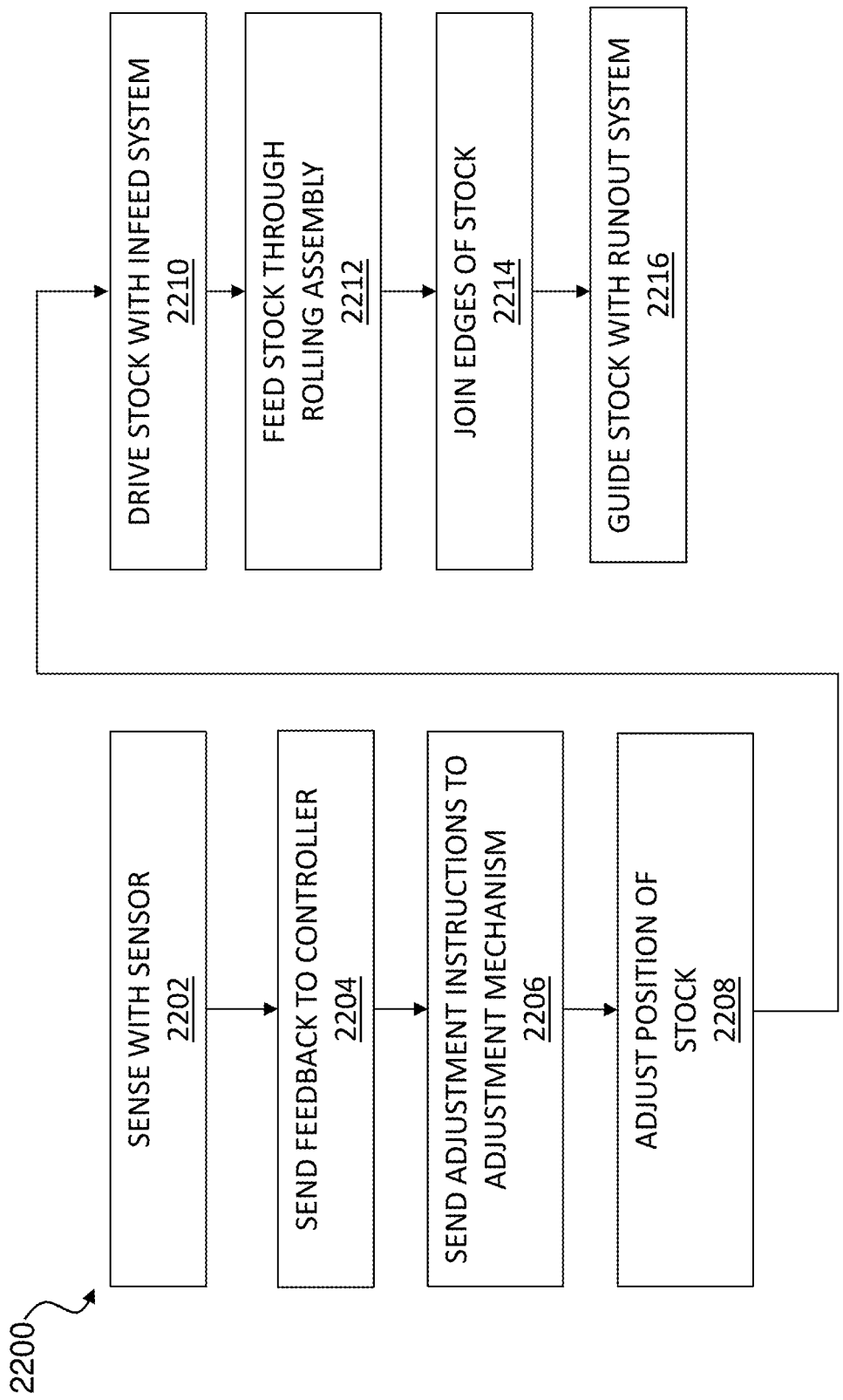
FIG. 22 is a flow chart of a method for forming a tapered structure.

FIG. 22 shows a method 2200 for forming a tapered structure.

As shown in step 2202, the method 2200 may include sensing, with a sensor, sensor data. The sensor data may include at least one of: a geometric attribute of the tapered structure being formed, a geometric attribute of a machine component, a force attribute of the tapered structure being formed, a force attribute of a machine component, a position of the stock of material, a position of a machine component, an inconsistency in a weld gap in the stock of material, a planar alignment error in the stock of material, and an angular alignment error in the stock of material. The sensing may take place at any step during the method shown 2200, and adjustments at any step may be made based in the sensor data.

As shown in step 2204, the method 2200 may include sending feedback from the sensor to a controller. The feedback may be based on the sensor data.

As shown in step 2206, the method 2200 may include sending adjustment instructions to the adjustment mechanism. The adjustment instructions may be sent from the controller, or from another component of the system. The adjustment instructions may be based on the feedback.

As shown in step 2208, the method 2200 may include adjusting a position of the stock of material using the adjustment mechanism based on the adjustment instructions. Adjusting the position of the stock of material may include the adjustment mechanism positioning at least one of: the infeed system, the at least three rolls, the runout system, and the tapered structure being formed.

As shown in step 2210, the method 2200 may include driving a stock of material with an infeed system. The infeed system may be any of the infeed systems described herein.

As shown in step 2212, the method 2200 may include feeding the stock of material through a rolling assembly. The rolling assembly may be any described herein, for example, a triple roll including at least three rolls with at least one bend roll and at least two guide rolls. The guide rolls may include rollette banks having a plurality of rollettes.

As shown in step 2214, the method 2200 may include joining edges of the stock of material together as the stock of material is rolled through the rolling assembly to form a tapered structure. The joining may utilize a joining element as described herein.

As shown in step 2216, the method 2200 may include guiding the stock of material out of the rolling assembly with a runout system. The runout system may be any of the runout systems described herein.

The control systems described herein include control systems directed to the entire construction system, or a portion thereof, including without limitation the infeed system, the curving device, the joining element, and the runout system. As used throughout this disclosure "control system" shall refer to a control system for any and all of the aforementioned systems, or combinations thereof, unless a particular component/machine is expressly required or otherwise clear from the context.

In the foregoing, the terms "machinery" and "component" refer to an element, or a combination of elements, of the construction system as described herein unless otherwise stated or clear from the context. These terms may also refer to the construction system as a whole.

The above control systems, devices, methods, processes, and the like may be realized in hardware, software, or any combination of these suitable for the control, data acquisition, and data processing described herein. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as the various systems described above, or all of the functionality may be integrated into a dedicated, standalone device. All such permutations and combinations are intended to fall within the scope of the present disclosure.

Embodiments disclosed herein may include computer program products comprising computer-executable code or computer-usable code that, when executing on one or more computing devices, performs any and/or all of the steps of the control systems described above. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the control systems described above may be embodied in any suitable transmission or propagation medium carrying computer-executable code and/or any inputs or outputs from same.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The meanings of method steps of the invention(s) described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

Described herein are systems, methods, and devices for constructing a tapered structure, and control systems and methods for same. It will be understood that while the exemplary embodiments herein emphasize the construction of a tapered structure and controls for same, the principles of the invention may be adapted to other fabrication processes. All such variations that can be adapted to use the systems, methods, and devices as described herein are intended to fall within the scope of this disclosure.

Other components of the control system may also be included, such as input devices including a keyboard, touchpad, mouse, switches, dials, buttons, and the like, as well as output devices such as a display, a speaker or other audio transducer, light emitting diodes, and the like. Other hardware may also or instead include a variety of cable connections and/or hardware adapters for connecting to, e.g., external computers, external hardware, external instrumentation or data acquisition systems, and the like.

The control systems may include, or be connected in a communicating relationship with, a network interface. The network interface may include any combination of hardware and software suitable for coupling the control system and construction system to a remote computer in a communicating relationship through a data network. By way of example and not limitation, this may include electronics for a wired or wireless Ethernet connection operating according to the IEEE 802.11 standard (or any variation thereof), or any other short or long range wireless networking components or the like. This may include hardware for short range data communications such as Bluetooth or an infrared transceiver, which may be used to couple into a local area network or the like that is in turn coupled to a data network such as the Internet. This may also or instead include hardware/software for a WiMax connection or a cellular network connection (using, e.g., CDMA, GSM, LTE, or any other suitable protocol or combination of protocols). Consistently, the control system may be configured to control participation by the construction system in any network to which the network interface is connected.

In the foregoing, various tasks have been described that involve relative motion of various components. However, it is recognized that varying design constraints or other practical considerations may call for certain components to remain fixed (relative to the ground) or to undergo only minimal motion. For example, the construction system can be designed such that any one or more of the following components remains fixed relative to the ground: the source of stock material, any desired component of the feed system, any desired component of the curving device, any desired component of the welder, any desired component of the runout system, the peak/top/end of the tapered structure under construction, etc. Similarly, the system can be designed such that none of the above components remain fixed relative to the ground (or, except as noted above, relative to each other). In some implementations, the heaviest or hardest to move component remains fixed relative to the ground. In some implementations, the relative motion of the components is chosen to best mitigate the risk of injury to those near the system. In some implementations, the relative motion of the components is chosen to maximize the expected life of the system as a whole or the expected life of one or more components.

While particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A control system for forming a tapered structure, the control system comprising:
a sensor arranged to measure a position of an edge of a stock material moving into a curving device for forming a tapered structure; and
a controller in communication with the sensor, the controller including one or more processors and non-transitory computer-readable storage media, the non-transitory computer-readable storage media having stored thereon instructions for causing the one or more processors to carry out processes including
receiving, from the sensor, a feedback signal indicative of the position of the edge of the stock material,
based on the feedback signal from the sensor, determining a control signal, and
sending the control signal to an infeed adjustment mechanism to position the stock material moving into at least one bend roll and at least two guide rolls of the curving device, the control signal moving the stock material about a peak of the tapered structure being formed as the stock material moves into the curving device.

2. The control system of claim 1, wherein the sensor includes a displacement sensor.

3. The control system of claim 1, wherein the control signal actuates at least one infeed actuator of the infeed adjustment mechanism to adjust an angle of the stock material moving into the curving device.

4. The control system of claim 1, wherein the control signal actuates an edge roller of the infeed adjustment mechanism to constrain positions of edge of the stock material moving into the curving device.

5. The control system of claim 1, wherein the instructions for causing the one or more processors to carry out determining the control signal include comparing the feedback signal from the sensor to a model for ideal edge positions of the stock material moving into the curving device.

6. The control system of claim 1, wherein the instructions for causing the one or more processors to carry out sending the control signal to the infeed adjustment mechanism to position the stock material includes continuously positioning the stock material as the stock material moves into the curving device for forming the tapered structure.

7. A control system for forming a tapered structure, the control system comprising:
a sensor arranged to measure position information of a stock material moving into a curving device; and
a controller in communication with the sensor, the controller including one or more processors and non-transitory computer-readable storage media, the non-transitory computer-readable storage media having stored thereon instructions for causing the one or more processors to carry out processes including
receiving the position information from the sensor,
receiving, from a model stored on the non-transitory computer-readable storage media, relative positions of the stock material moving into the curving device,
determining a control signal based on the model and the position information of the stock material measured by the sensor, and
sending the control signal to an infeed adjustment mechanism to position the stock material moving into at least three rolls including at least one bend roll and at least two guide rolls of the curving device, the control signal moving the stock material about a peak of the tapered structure being formed as the stock material moves into the curving device.

8. The control system of claim 7, wherein the sensor includes a displacement sensor.

9. The control system of claim 7, wherein the rotational motion of the stock material about the peak of the tapered structure being formed adjusts for irregularity in shape of the stock material moving into the curving device.

10. The control system of claim 7, wherein the relative positions of the stock material moving into the curving device include ideal edge positions of the stock material moving into the curving device.

11. The control system of claim 7, wherein the instructions for causing the one or more processors to carry out processes including sending the control signal to the infeed adjustment mechanism include instructions for causing the one or more processors to carry out processes including actuating at least one infeed actuator of the infeed adjustment mechanism to adjust an angle of the stock material moving into the curving device.

12. The control system of claim 7, wherein the instructions for causing the one or more processors to carry out processes including sending the control signal to the infeed adjustment mechanism include instructions for causing the one or more processors to adjust an infeed speed of the stock material moving into the curving device.

13. The control system of claim 7, wherein the instructions for causing the one or more processors to carry out processes including sending the control signal to the infeed adjustment mechanism include differentially driving infeed rollers of the infeed adjustment mechanism.

* * * * *